United States Patent
Takaoka et al.

(10) Patent No.: US 9,122,016 B2
(45) Date of Patent: Sep. 1, 2015

(54) OPTICAL MEASUREMENT APPARATUS AND PROBE APPARATUS

(71) Applicant: OLYMPUS CORPORATION, Tokyo (JP)

(72) Inventors: Hideyuki Takaoka, Hachioji (JP); Yuki Shono, Hachioji (JP); Ryosuke Ito, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 202 days.

(21) Appl. No.: 13/869,631

(22) Filed: Apr. 24, 2013

(65) Prior Publication Data
US 2013/0329224 A1    Dec. 12, 2013

Related U.S. Application Data

(63) Continuation of application No. PCT/JP2011/074568, filed on Oct. 25, 2011.

(60) Provisional application No. 61/408,190, filed on Oct. 29, 2010.

(51) Int. Cl.
*G01N 21/47* (2006.01)
*G02B 6/35* (2006.01)
(Continued)

(52) U.S. Cl.
CPC .............. *G02B 6/35* (2013.01); *A61B 1/00096* (2013.01); *A61B 1/00167* (2013.01);
(Continued)

(58) Field of Classification Search
CPC ................... G02B 6/35; G01N 21/474; G01N 2021/4709; G01N 2021/4745; A61B 1/0096; A61B 1/0067; A61B 1/0669; A61B 1/07; A61B 5/0084

USPC ............ 385/12, 16; 606/15, 16; 356/402, 446
See application file for complete search history.

(56) References Cited

U.S. PATENT DOCUMENTS

| 4,669,467 | A | 6/1987 | Willett et al. |
| 7,623,907 | B2 * | 11/2009 | Takaoka et al. .............. 600/476 |

(Continued)

FOREIGN PATENT DOCUMENTS

| JP | A-9-117407 | 5/1997 |
| JP | A-2001-157660 | 6/2001 |

(Continued)

OTHER PUBLICATIONS

International Search Report issued in International Patent Application No. PCT/JP2011/074568 mailed Dec. 6, 2011.

*Primary Examiner* — Daniel Petkovsek
(74) *Attorney, Agent, or Firm* — Oliff PLC

(57) ABSTRACT

An optical measurement apparatus that measures an optical property of a scattering medium includes a light source that supplies illumination light having at least one spectral component, an illumination fiber for guiding the light supplied by the light source and emitting the light to the scattering medium, a detection fiber for receiving returned light from the scattering medium at a tip thereof and guiding the returned light toward a base end thereof, a detecting unit that detects light output from the base end of the detection fiber, a measuring unit that measures a property of the scattering medium based on a detection result obtained by the detecting unit, and a switching unit that switches between total areas of emission regions, in which light is emitted, at an end face of the illumination fiber.

27 Claims, 25 Drawing Sheets

(51) Int. Cl.
- *A61B 1/00* (2006.01)
- *A61B 1/07* (2006.01)
- *A61B 5/00* (2006.01)
- *A61B 1/06* (2006.01)

(52) U.S. Cl.
CPC ............... *A61B 1/0669* (2013.01); *A61B 1/07* (2013.01); *A61B 5/0084* (2013.01); *G01N 21/474* (2013.01); *G01N 2021/4709* (2013.01); *G01N 2021/4745* (2013.01)

(56) References Cited

U.S. PATENT DOCUMENTS

| | | | |
|---|---|---|---|
| 7,652,772 | B2 | 1/2010 | Backman et al. |
| 7,652,881 | B1 | 1/2010 | Sun |
| 7,952,719 | B2 * | 5/2011 | Brennan, III ................ 356/479 |
| 8,830,460 | B2 * | 9/2014 | Shono et al. .................. 356/337 |
| 8,836,939 | B2 * | 9/2014 | Gono ......................... 356/243.1 |
| 2005/0054937 | A1 | 3/2005 | Takaoka et al. |
| 2006/0013544 | A1 | 1/2006 | Bouma et al. |
| 2008/0037024 | A1 | 2/2008 | Backman et al. |
| 2008/0304074 | A1 | 12/2008 | Brennan, III |
| 2009/0003759 | A1 | 1/2009 | Boyd |
| 2009/0009759 | A1 | 1/2009 | Backman et al. |

FOREIGN PATENT DOCUMENTS

| | | |
|---|---|---|
| JP | A-2001-269312 | 10/2001 |
| JP | A-2005-40175 | 2/2005 |
| JP | A-2008-506426 | 3/2008 |
| JP | A-2009-537014 | 10/2009 |
| JP | A-2010-63839 | 3/2010 |
| JP | A-2010-529465 | 8/2010 |
| WO | WO 2007/133684 A2 | 11/2007 |

* cited by examiner

OPTICAL MEASUREMENT APPARATUS AND PROBE APPARATUS

CROSS-REFERENCE TO RELATED APPLICATIONS

This application is a continuation of PCT international application Ser. No. PCT/JP2011/074568 filed on Oct. 25, 2011 which designates the United States, incorporated herein by reference, and which claims the benefit of priority from U.S. Provisional Patent Application No. 61/408,190, filed on Oct. 29, 2010, incorporated herein by reference.

BACKGROUND OF THE INVENTION

1. Field of the Invention

The present invention relates to an optical measurement apparatus and a measurement probe apparatus for measuring the optical property of a scatterer.

2. Description of the Related Art

In recent years, an optical measurement apparatus using a LEBS (Low-Coherence Enhanced Backscattering) technology has been proposed that detects the property of a scattering medium by applying incoherent light with a short spatial coherence length to the scattering medium from a tip of a probe and measuring scattered light (see, for example, International Publication No. WO 2007/133684, US Patent Application Publication No. 2008/0037024, U.S. Pat. No. 7,652,772, and US Patent Application Publication No. 2009/0009759). Such an optical measurement apparatus can perform optical measurement on an object, such as a tissue, being a scattering medium, in combination with an endoscope that observes an organ, such as a digestive organ.

SUMMARY OF THE INVENTION

In accordance with some embodiments, an optical measurement apparatus and a measurement probe apparatus for measuring the optical property of a scattering medium are presented.

In some embodiments, an optical measurement apparatus that measures an optical property of a scattering medium includes a light source that supplies illumination light having at least one spectral component, an illumination fiber for guiding the light supplied by the light source and emitting the light to the scattering medium, a detection fiber for receiving returned light from the scattering medium at a tip thereof and guiding the returned light toward a base end thereof, a detecting unit that detects light output from the base end of the detection fiber, a measuring unit that measures a property of the scattering medium based on a detection result obtained by the detecting unit, and a switching unit that switches between total areas of emission regions, in which light is emitted, at an end face of the illumination fiber.

In some embodiments, an optical measurement apparatus that measures an optical property of a scattering medium includes a main body device and a probe that is detachably connected to the main body device and that is insertable into a body. The main body device includes: a light source that supplies illumination light having at least one spectral component; a detecting unit that detects light output by the probe; and a measuring unit that measures a property of the scattering medium based on a detection result obtained by the detecting unit. The probe includes: a plurality of shared fibers, each having an incident-emission region with a different area for inputting and outputting light at an end face thereof; and a connecting unit that is inserted into an insertion port of the main body device to connect an output portion of the main body device, at which the light supplied by the light source is output, and a base end of one of the shared fibers, and to connect a base end of the other shared fiber and an input portion of the main body device, at which light is input toward the detecting unit. An orientation of a contact face of the connecting unit being in contact with the output portion and the input portion of the main body device is changeable to switch between the shared fiber connected to the output portion of the main body device at which the light supplied by the light source is output and the shared fiber connected to the input portion of the main body device at which the light is input toward the detecting unit.

In some embodiments, a measurement probe apparatus is detachably connected to an optical measurement apparatus that measures a property of a scattering medium. The measurement probe apparatus includes: an illumination fiber for guiding light supplied by an external apparatus and emitting the light to the scattering medium; a detection fiber for receiving returned light from the scattering medium at a tip of thereof and guiding the returned light to a base end thereof; and a switching unit that switches between total areas of emission regions, in which light is emitted, at an end face of the illumination fiber.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of an optical measurement apparatus and a probe according to the present invention will be explained in detail below with reference to the accompanying drawings. The present invention is not limited by the embodiments below. In the descriptions of the drawings, the same components are denoted by the same symbols. It should be noted that the drawings are schematic illustrations and relations between thicknesses and widths of components or the proportions of the components may differ from actual ones. Furthermore, some relations of the dimensions or the proportions of the components may differ between the drawings.

First Embodiment

Figure 1:
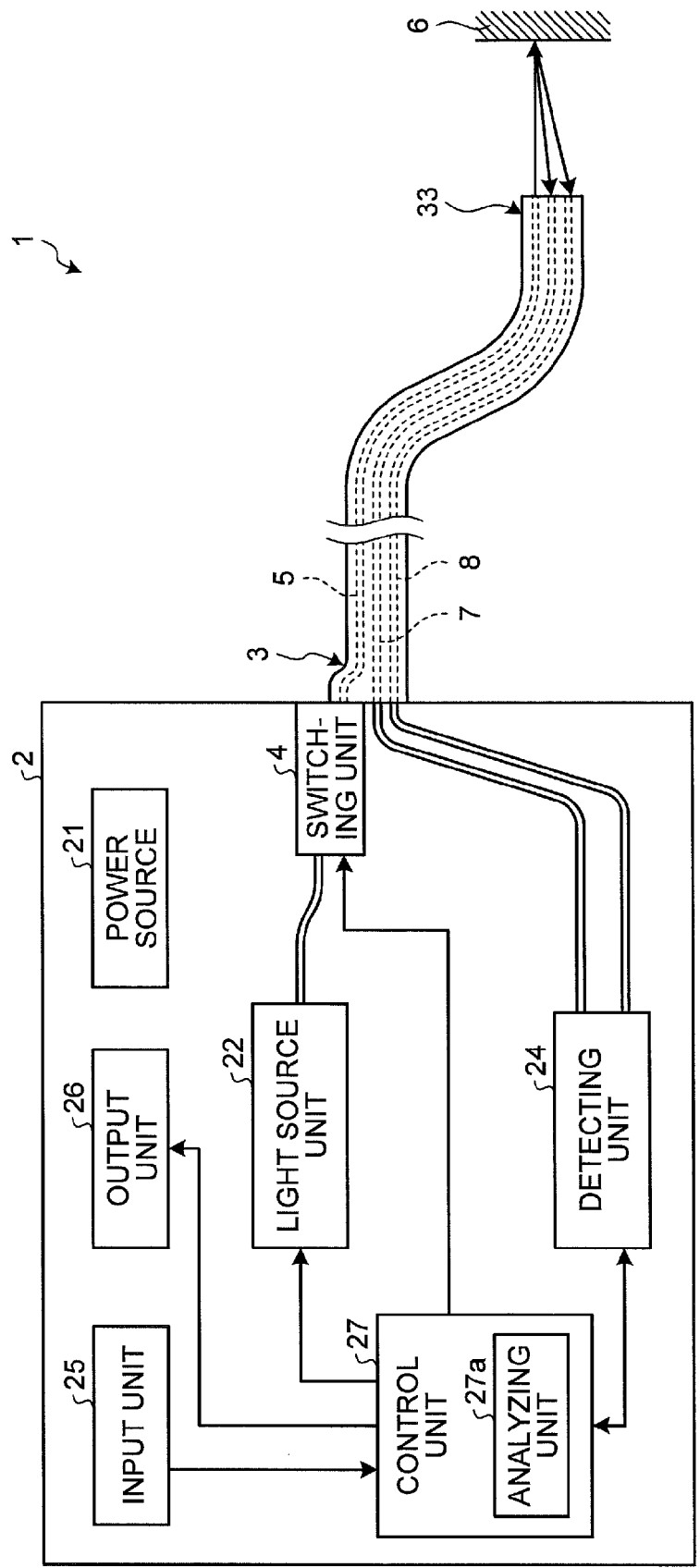
FIG. 1 is a schematic diagram of an overall configuration of an optical measurement apparatus according to a first embodiment.

FIG. 1 is a schematic diagram of an overall configuration of an optical measurement apparatus according to a first embodiment of the present invention. As illustrated in FIG. 1, an optical measurement apparatus 1 according to the first embodiment includes a main unit 2 that performs optical measurement on an object 6, such as a tissue, being a scattering medium to detect the property of the object; and a measurement probe 3 that is inserted into a subject. The probe 3 is detachably connected to the main unit 2 at a base end thereof, emits light that is supplied, via the base end, by the connected main unit 2 to the object 6 via a tip thereof, and outputs scattered light that comes, via a tip portion 33, from the object 6 to the main unit 2 via the base end.

The main unit 2 includes a power source 21, a light source unit 22, a detecting unit 24, an input unit 25, an output unit 26, and a control unit 27.

The power source 21 supplies power to components of the main unit 2.

The light source unit 22 emits light for illuminating the object 6. The light source unit 22 is realized by an incoherent optical source, such as a white LED (Light Emitting Diode), a xenon lamp, or a halogen lamp, and one or more lenses. The light source unit 22 supplies, to the probe 3, incoherent light for illuminating an object.

The detecting unit 24 detects, as detected light, light that is scattered from the object 6 and output by the probe 3. The detecting unit 24 is realized by a spectroscope. The detecting unit 24 measures a spectral component or the intensity of the scattered light output by the probe 3 and performs measurement at each wavelength. The detecting unit 24 outputs a measurement result to the control unit 27.

The input unit 25 is realized by a push switch or the like, and upon operation of the switch or the like, receives instruction information for giving an instruction to activate the main unit 2 or other types of instruction information and inputs the information to the control unit 27.

The output unit 26 outputs information on various processes of the optical measurement apparatus 1. The output unit 26 is realized by a display, a speaker, a motor, or the like, and outputs image information, voice information, or vibration to thereby output the information on the various processes of the optical measurement apparatus 1.

The control unit 27 controls process operations of the components of the main unit 2. The control unit 27 is realized by a CPU (Central Processing Unit) and a semiconductor memory, such as a RAM (Random Access Memory). The control unit 27 transfers instruction information or data to the components of the main unit 2 to thereby control the operations of the main unit 2. The control unit 27 includes an analyzing unit 27a that analyzes the property of the object 6 based on a detection result obtained by the detecting unit 24. In other words, the analyzing unit 27a functions as a measuring unit.

The probe 3 is realized by one or more optical fibers. For example, the probe 3 includes an illumination fiber 5 for guiding light supplied by the light source and emitting the light to the object 6; and detection fibers 7 and 8 for receiving returned light from the object 6 at tips thereof and guiding the light toward base ends. When the LEBS technology is used, at least two beams of scattered light having different scattering angles are received; therefore, detection fibers 7 and 8 are provided.

The main unit 2 further includes a switching unit 4 that switches a total area of an emission region, in which light is emitted, at an end face of the illumination fiber 5. The main unit 2 can change the total area of the emission region in which light is emitted at the end face of the illumination fiber 5. That enables setting a spatial coherence length of illumination light suited to the object 6.

Figure 2:
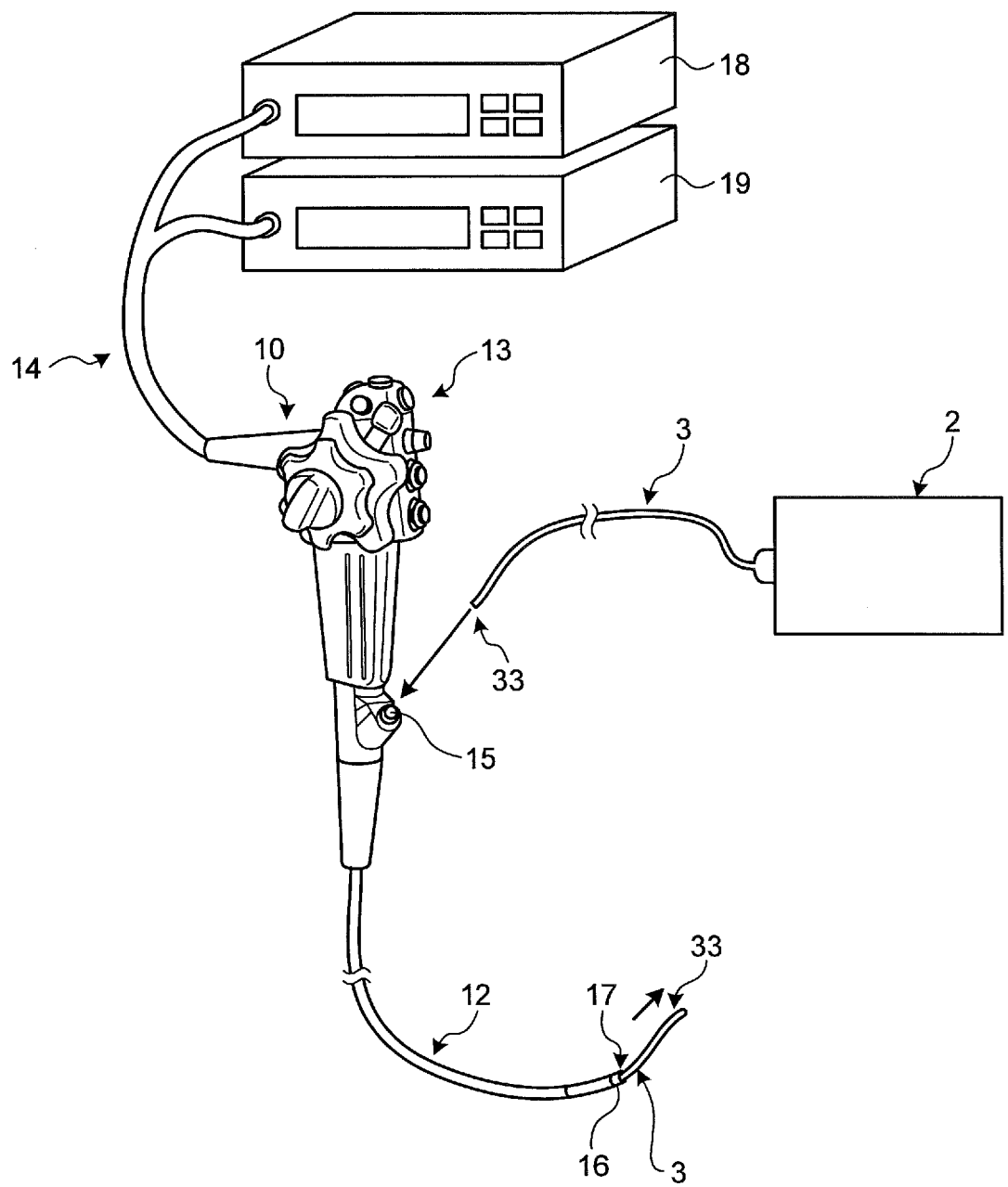
FIG. 2 is a diagram for explaining insertion of a probe illustrated in FIG. 1 into a subject.

The optical measurement apparatus 1 performs optical measurement in combination with an endoscope that observes an organ, such as a digestive organ. FIG. 2 is a diagram illustrating a configuration of a test system and attachment of the probe 3. In FIG. 2, a flexible universal cord 14 that has a side portion of an operating unit 13 is connected to a light source device 18 and to a signal processing device 19 that performs a process on an image of an object captured at a tip portion 16 of an endoscope 10. The probe 3 is inserted from a probe channel insertion port 15 near the operating unit 13 that is located outside the body while the endoscope 10 is inserted in a subject. The tip portion 33 of the probe 3 protrudes from an opening 17 of the tip portion 16 that is connected to the probe channel through the inside of an insertion portion 12. Accordingly, the probe 3 is inserted into the subject and the optical measurement apparatus 1 starts optical measurement.

Figure 3:
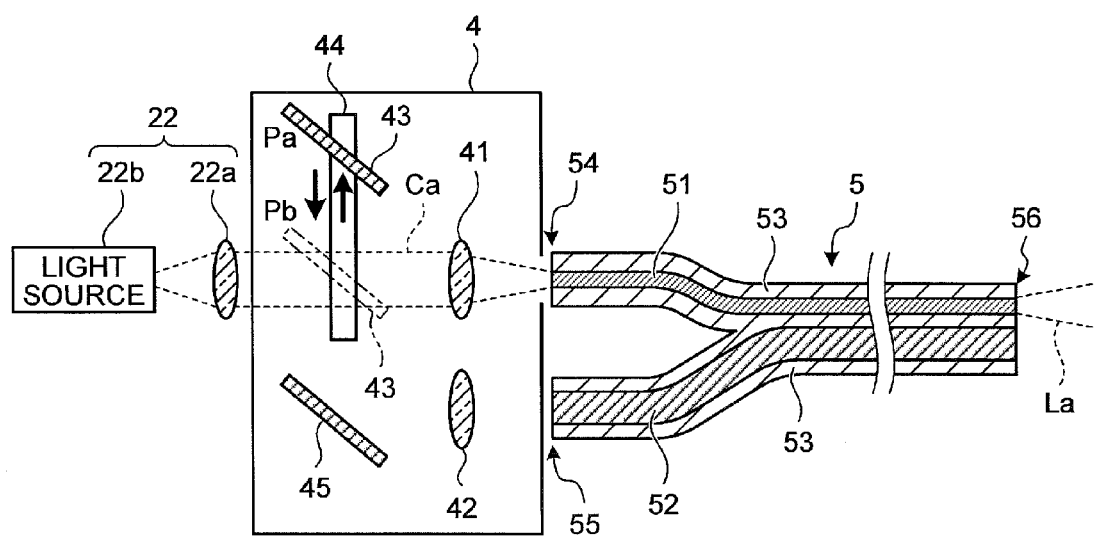
FIG. 3 is a diagram for explaining a switching unit and an illumination fiber of the probe illustrated in FIG. 1.
Figure 4:
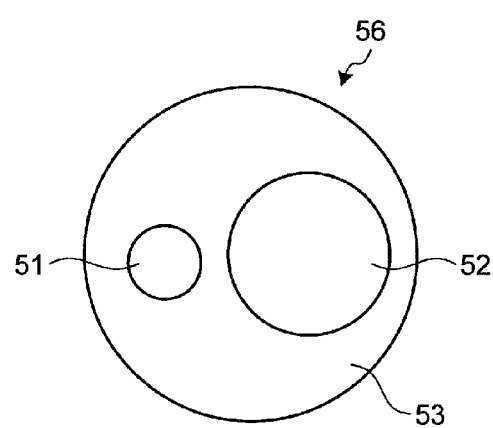
FIG. 4 is a diagram illustrating an end face of the illumination fiber illustrated in FIG. 3.

The switching unit 4 and the illumination fiber 5 of the probe 3 will be explained below. FIG. 3 is a cross-sectional view of the switching unit 4 and the illumination fiber 5 of the probe 3 illustrated in FIG. 1, taken along an optical axis. FIG. 4 is a diagram illustrating an end face 56 of the illumination fiber 5 illustrated in FIG. 3.

As illustrated in FIG. 3 and FIG. 4, the illumination fiber 5 includes a first core 51 that functions as a first light guide; a second core 52 that functions as a second light guide; and a cladding 53 that surrounds the cores. A core diameter of the first core 51 and a core diameter of the second core 52 differ from each other. As illustrated in FIG. 4, areas of emission regions for emitting light at the end face 56 differ between the first core 51 and the second core 52. For example, in the example illustrated in FIG. 3 and FIG. 4, the area of the emission region of the second core 52 at the end face 56 is greater than that of the first core 51. The illumination fiber 5 is bifurcated at the base end such that a base end of the first core 51 is located at one bifurcated base end 54 and a base end of the second core 52 is located at the other bifurcated base end 55.

The switching unit 4 switches a region, in which light supplied by a light source 22b of the light source unit 22 via a lens 22a is input, to the first core 51 on the base end 54 of the illumination fiber 5 or to the second core 52 on the base end 55 of the illumination fiber 5. The switching unit 4 switches a path of the light supplied by the light source unit 22 to a path Ca reaching the base end 54 of the illumination fiber 5 or to a path Cb reaching the base end 55 of the illumination fiber 5 (see FIG. 5).

The switching unit 4 includes a mirror 43; and a moving system 44 that moves the mirror 43 to a position Pa outside the path Ca or a position Pb inside the path Ca. The moving system 44 is a sliding system that can determine the position of the mirror 43 to the position Pa or the position Pb, and moves the mirror 43 due to sliding caused by an external force.

As illustrated in FIG. 3, when the moving system 44 moves the mirror 43 to the position Pa, light supplied by the light source unit 22 passes through the path Ca as it is and reaches the base end 54 of the illumination fiber 5 via a lens 41. As a result, light La is emitted from the first core 51 at the end face 56 of the illumination fiber 5.

Figure 5:
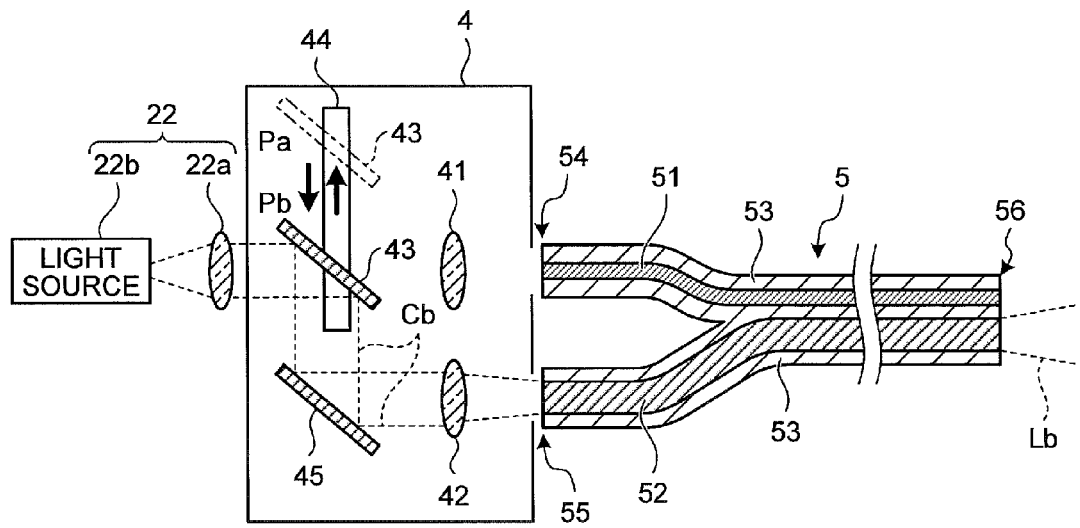
FIG. 5 is another diagram for explaining the switching unit and the illumination fiber of the probe illustrated in FIG. 1.

On the other hand, as illustrated in FIG. 5, when the moving system 44 moves the mirror 43 to the position Pb, light supplied by the light source unit 22 is reflected by the mirror 43 located at the position Pb toward a mirror 45, is further reflected by the mirror 45 toward a lens 42, and reaches the base end 55 of the illumination fiber 5 via the lens 42. As a result, light Lb is emitted from the second core 52 that has a greater area of the emission region than the first core 51 at the end face 56 of the illumination fiber 5.

The spatial coherence length of illumination light is obtained such that $(\lambda \cdot S)/(\pi \cdot D)$, where $\lambda$ is the wavelength of light, S is a distance from a light emitting face of the illumination fiber to an object, and D is a core diameter of the fiber.

Therefore, when the switching unit 4 switches the path of the light supplied by the light source unit 22 to the path Ca in order to emit the light from the first core 51 having a smaller core diameter than that of the second core 52, it becomes possible to perform illumination with a longer spatial coherence length than that obtained when the path is switched to the path Cb. In other words, when the switching unit 4 switches the path of the light supplied by the light source unit 22 to the path Cb in order to emit the light from the second core 52 having a greater core diameter than that of the first core, it becomes possible to perform illumination with a shorter spatial coherence length than that obtained when the path is switched to the path Ca.

Furthermore, when a half mirror is disposed at the position Pb instead of the mirror 43, the light supplied by the light source unit 22 is guided to both the path Ca and the path Cb and enters both the first core 51 at the base end 54 and the second core 52 at the base end 55. As a result, the light is emitted from both of the first core 51 and the second core 52 at the end face 56 of the illumination fiber 5. In this case, the light emission region becomes greater than the case that the light is emitted from either the first core 51 or the second core 52. Therefore, the spatial coherence length of the light applied to an object becomes shorter than the spatial coherence length of the light emitted from only the second core 52.

Therefore, by causing the switching unit 4 to switch between the optical paths and by selecting the type of the mirror 43 of the switching unit 4, it is possible to select three different spatial coherence lengths as the spatial coherence length of the light applied to the object 6.

In this way, according to the first embodiment, it is possible to perform illumination with a plurality of spatial coherence lengths by one probe. Therefore, according to the first embodiment, it is possible to change the spatial coherence length of illumination light by only switching the position of the mirror 43 of the switching unit 4 without interchanging probes having illumination fibers with different core diameters in accordance with an object during measurement.

The moving system 44 may be a sliding system that includes a motor for moving the mirror, that moves the mirror 43 by causing the control unit 27 to control the motor, that can determine the position of the mirror to either the position Pa or the position Pb, and that moves the mirror 43 due to sliding caused by an external force.

Second Embodiment

Figure 6:
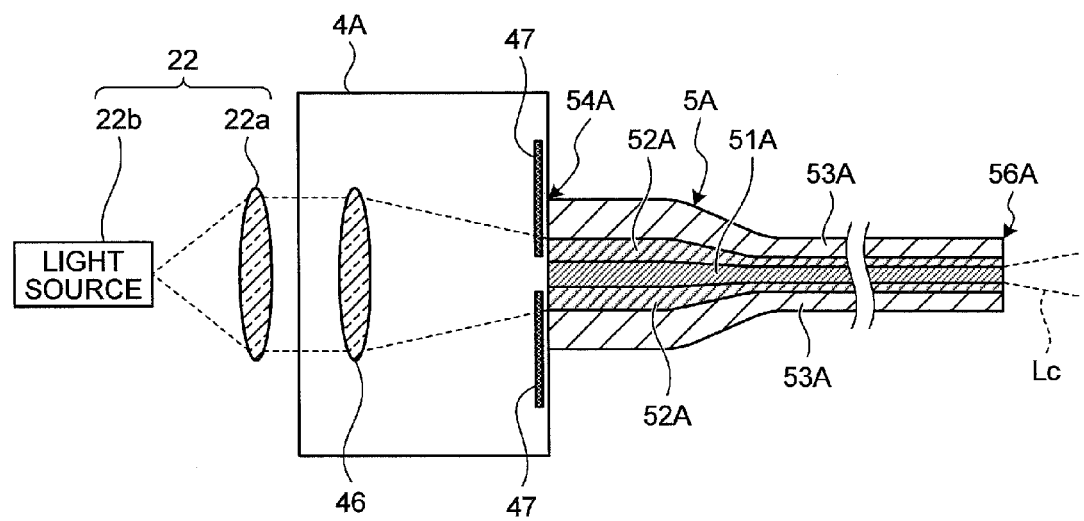
FIG. 6 is a diagram for explaining a switching unit and an illumination fiber of a probe according to a second embodiment.
Figure 7:
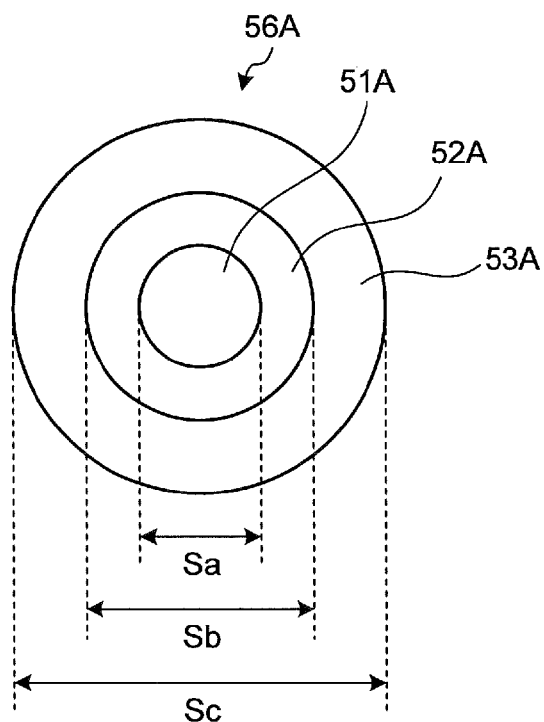
FIG. 7 is a diagram illustrating an end face of the illumination fiber illustrated in FIG. 6.

A second embodiment will be explained below. FIG. 6 is a diagram for explaining a switching unit and an illumination fiber of a probe according to the second embodiment. Components of an optical measurement apparatus according to the second embodiment are the same as those of the first embodiment. FIG. 6 is a cross-sectional view of the switching unit and the illumination fiber of the probe according to the second embodiment, taken along an optical axis. FIG. 7 is a diagram illustrating an end face of the illumination fiber illustrated in FIG. 6.

As illustrated in FIG. 6 and FIG. 7, in the second embodiment, an illumination fiber 5A is a double cladding fiber that includes a core 51A located in a center region Sa; a first cladding 52A formed in a region Sb surrounding the core 51A; and a second cladding 53A formed in a region Sc surrounding the first cladding 52A. A base end 54A of the illumination fiber 5A is formed such that the entire diameter of the illumination fiber 5A at the base end 54A becomes thicker than the entire diameter of a tip at which an end face 56A is located.

Figure 8:
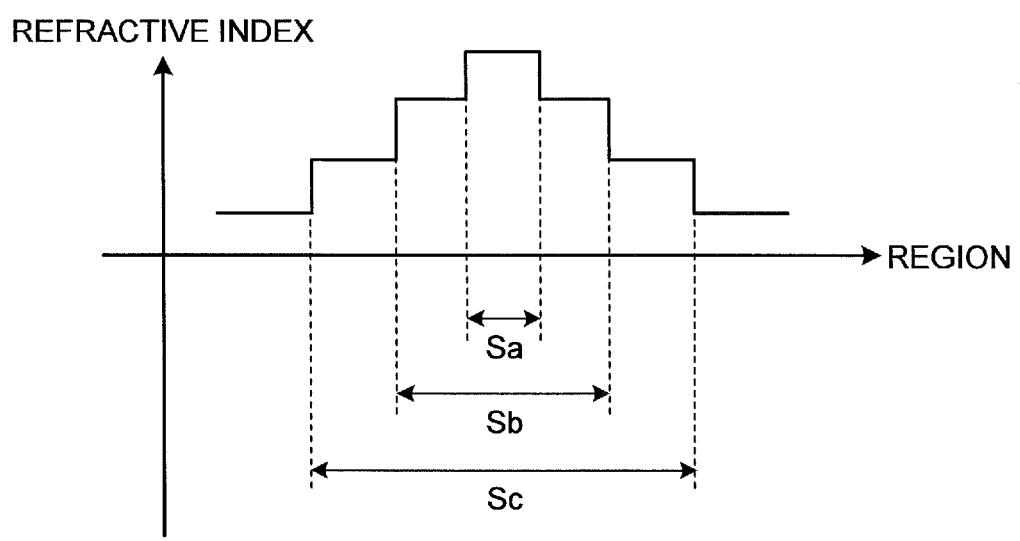
FIG. 8 is a diagram illustrating a magnitude correlation of the refractive indices of a core, a first cladding, and a second cladding illustrated in FIG. 6.

FIG. 8 is a diagram illustrating a magnitude correlation of the refractive indices of the core 51A, the first cladding 52A, and the second cladding 53A illustrated in FIG. 6. As illustrated in FIG. 8, the refractive index of the core 51A in the region Sa is the highest, and the refractive index is lowered step by step toward the outer circumference of the illumination fiber in the order of the first cladding 52A in the region Sb and the second cladding 53A in the region Sc. Therefore, light that is input to only the core 51A at the base end 54A of the illumination fiber 5A propagates through only the core 51A, and light that is input to both the core 51A and the first cladding 52A at the base end 54A of the illumination fiber 5A propagates through both regions of the core 51A and the first cladding 52A.

A switching unit 4A switches a region, in which light supplied by the light source 22b via the lens 22a is input, to the core 51A of the base end 54A of the illumination fiber 5A or to both of the first core 51A and the first cladding 52A, at the base end of the illumination fiber 5A.

As illustrated in FIG. 6, the switching unit 4A includes a lens 46 that focuses the light supplied by the light source 22b via the lens 22a onto both regions of the core 51A and the first cladding 52A at the base end 54A of the illumination fiber 5A; and an attachable-detachable diaphragm 47. The diaphragm 47 includes an opening with a diameter that is the same as or slightly smaller than the diameter of the core 51A of the base end 54A so that the light can be emitted to only the core 51A of the base end 54A of the illumination fiber 5A.

As illustrated in FIG. 6, when the diaphragm 47 is attached to the switching unit 4A, light supplied by the light source unit 22 is collected by the lens 46 and the amount of the light is adjusted by the diaphragm 47, so that the light is input to only the core 51A of the base end 54A of the illumination fiber 5A. As a result, the light input to the core 51A propagates through the core 51A and is emitted as light Lc from the region Sa occupied by the core 51 at the end face 56A.

Figure 9:
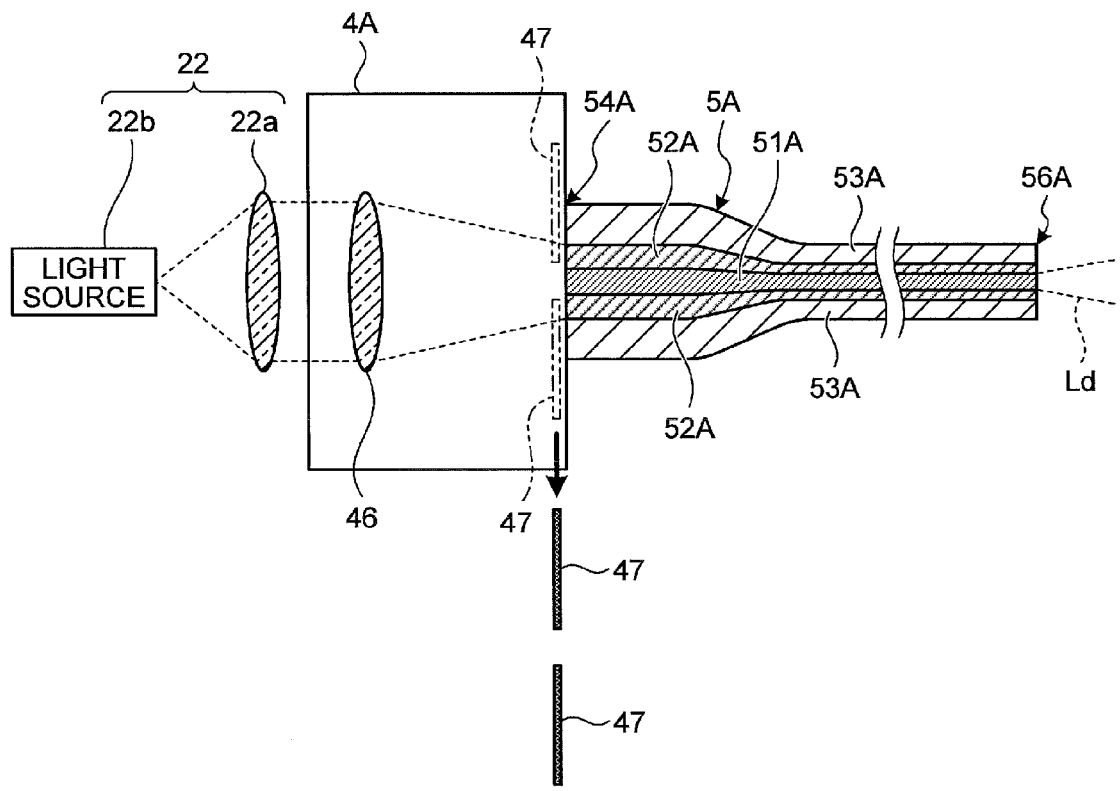
FIG. 9 is another diagram for explaining the switching unit illustrated in FIG. 7.

On the other hand, as illustrated in FIG. 9, when the diaphragm 47 is detached from the switching unit 4A, light supplied by the light source unit 22 is collected by the lens 46 and is input to the core 51A and the first cladding 52A at the base end 54A of the illumination fiber 5A as it is. As a result, the light input to the core 51A and the first cladding 52A propagates through both the core 51A and the first cladding 52A and is emitted as light Ld from the region Sa occupied by the core 51A and the region Sb occupied by the first cladding 52A at the end face 56A.

Therefore, when the diaphragm 47 is attached to the switching unit 4A to emit light only from the core 51A, it becomes possible to perform illumination with a longer spatial coherence length than that obtained when the diaphragm 47 is detached from the switching unit 4A. In other words, when the diaphragm 47 is detached from the switching unit 4A to emit light from the core 51A and the first cladding 52A, it becomes possible to perform illumination with a shorter spatial coherence length than that obtained when the diaphragm 47 is attached to the switching unit 4A.

As in the second embodiment, even when the double cladding fiber is used as the illumination fiber and the region in which the light supplied to the illumination fiber is changed, similarly to the first embodiment, it is possible to perform illumination with a plurality of spatial coherence lengths by one probe.

Figure 10:
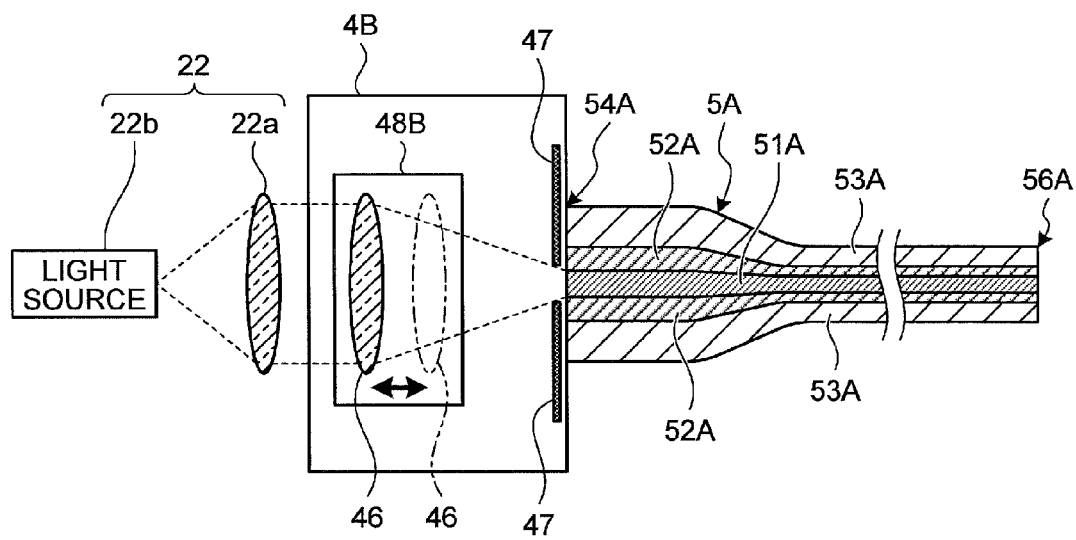
FIG. 10 is a diagram for explaining another example of the switching unit illustrated in FIG. 7.

In the second embodiment, as illustrated in FIG. 10, it may be possible to use a switching unit 4B, instead of the switching unit 4A, that includes a moving system 48B capable of moving the lens 46 along the optical axis as indicated by an arrow. By causing the moving system 48B to adjust the position of the lens 46 on the optical axis so that the light is condensed on the core 51A while the diaphragm 47 is attached, it becomes possible to improve the use efficiency of the light.

Figure 11:
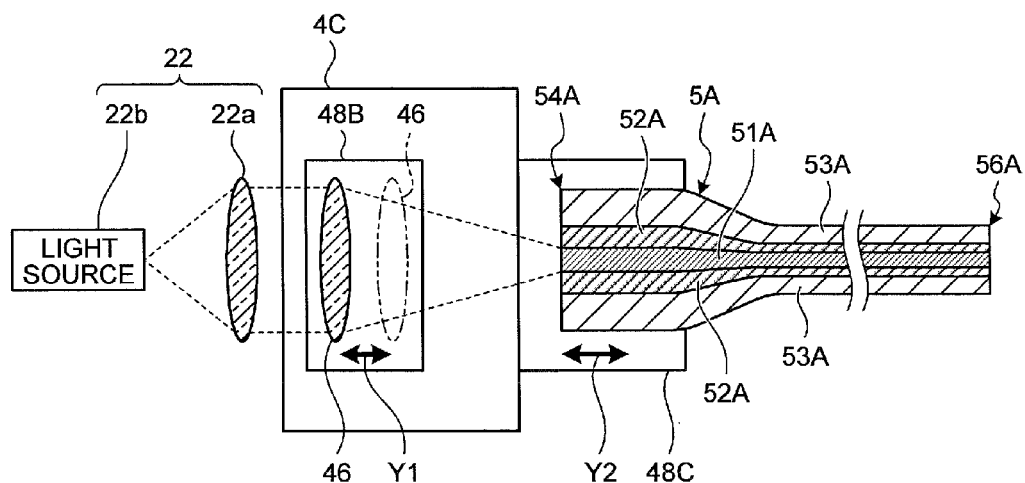
FIG. 11 is a diagram for explaining another example of the switching unit illustrated in FIG. 7.

It is sufficient that a relative distance between the lens 46 and the base end 54A of the illumination fiber 5A; therefore, as illustrated in FIG. 11, it may be possible to provide a moving system 48C that can move the base end 54A of the illumination fiber 5A along the optical axis. In this case, the moving system 48B of a switching unit 4C adjusts the position of the lens 46 on the optical axis as indicated by an arrow Y1, and the moving system 48C adjusts the position of the base end 54A of the illumination lens 5A on the optical axis as indicated by an arrow Y2. Therefore, it becomes possible to select an incident region at the base end 54A for inputting the light supplied by the light source unit 22 in accordance with a desired spatial coherence length. In this case, it is possible to omit the diaphragm 47. Furthermore, the incident region at the base end 54A for inputting the light supplied by the light source unit 22 can be selected by changing the relative distance between the lens 46 and the base end 54A of the illumination fiber 5A; therefore, it is sufficient that the switching unit 4C includes one of the diaphragm 47, the moving system 48B, and the moving system 48C.

Figure 12:
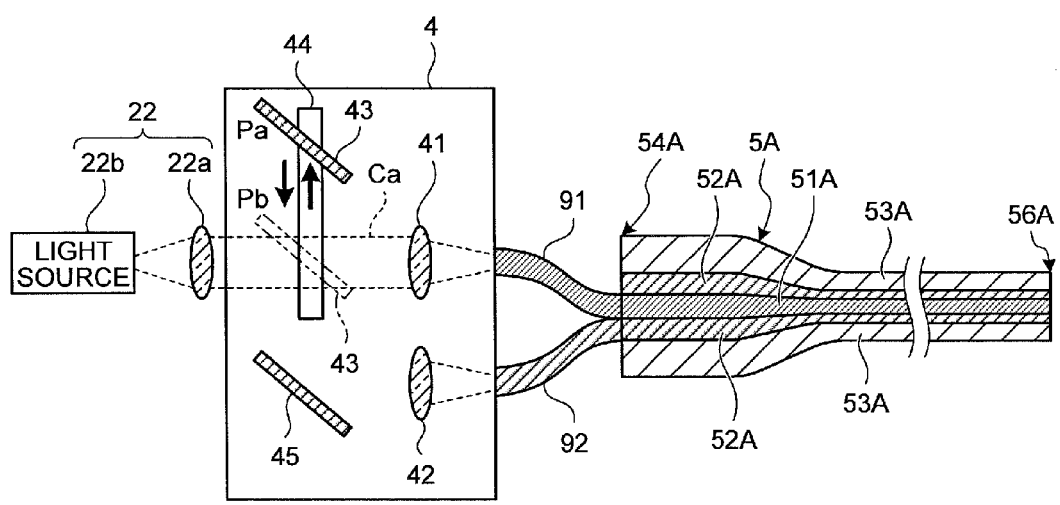
FIG. 12 is a schematic diagram of another overall configuration of the optical measurement apparatus according to the second embodiment.

Furthermore, in the second embodiment, it is possible to use the switching unit 4 illustrated in FIG. 3 instead of the switching unit 4A, 4B, or 4C. In this case, as illustrated in FIG. 12, at the base end 54A of the illumination fiber 5A, the path Ca and the core 51A are connected to each other with a connection fiber 91, and the path Cb and the first cladding 52A are connected to each other with a connection fiber 92. The switching unit 4 switches the optical path to the path Ca or the path Cb by moving the mirror 43 to thereby switch the incident region at the base end 54A for inputting the light supplied by the light source unit 22.

Third Embodiment

Figure 13:
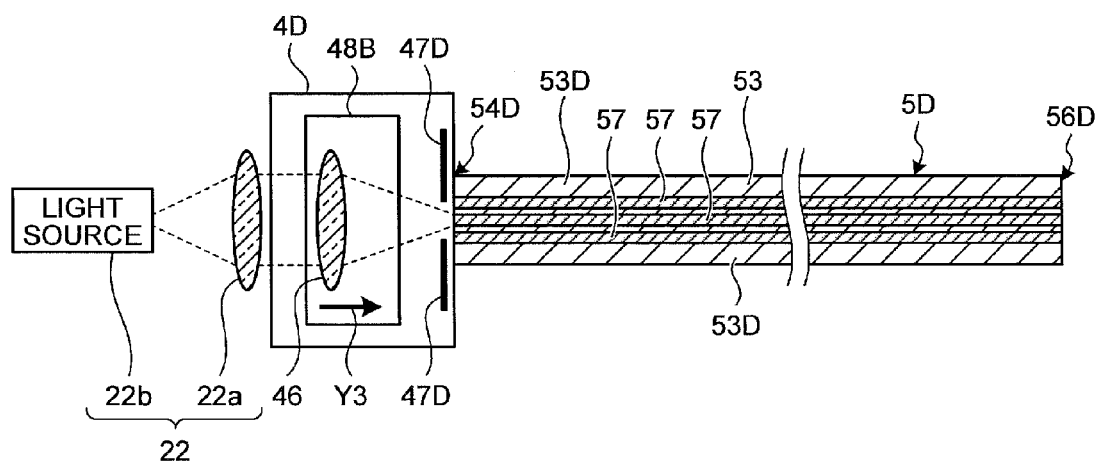
FIG. 13 is a diagram for explaining a switching unit and an illumination fiber of a probe according to a third embodiment.
Figure 14:
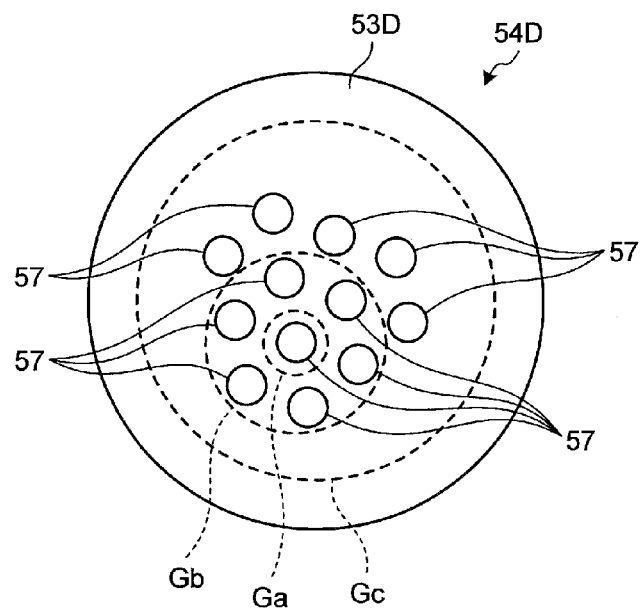
FIG. 14 is a diagram illustrating an end face of the illumination fiber illustrated in FIG. 13.

A third embodiment will be explained below. FIG. 13 is a diagram for explaining a switching unit and an illumination fiber of a probe according to the third embodiment. Components of an optical measurement apparatus according to the third embodiment are the same as those of the first embodiment. FIG. 13 is a cross-sectional view of the switching unit and the illumination fiber of the probe according to the third embodiment, taken along the optical axis. FIG. 14 is a diagram illustrating an end face 56D of an illumination fiber 5D illustrated in FIG. 13.

As illustrated in FIG. 13 and FIG. 14, the illumination fiber 5D according to the third embodiment is a multicore fiber, in which a plurality of cores 57 are disposed inside a cladding 53D. A switching unit 4D according to the third embodiment includes an adjustable diaphragm 47D instead of the diaphragm 47 of the switching unit 4B illustrated in FIG. 10.

The switching unit 4D switches a region, in which light supplied by the light source unit 22 is input at a base end 54D of the illumination fiber 5D, to one of the cores 57 of the illumination fiber 5D or to one of a plurality of core groups, each including a different combination of a plurality of adjacent cores 57 of the illumination fiber 5D. For example, as illustrated in FIG. 14, an example will be explained in which the cores 57 used for illumination are grouped into a core region Ga containing only one of the cores 57, a core region Gb containing a plurality of the cores 57 surrounding the core region Ga, and a core region Gc containing a plurality of the cores 57 surrounding the core region Gb.

When illumination is performed with the longest spatial coherence length, the moving system 48B moves the position of the lens 46 on the optical axis toward the light source unit 22 side as illustrated in FIG. 13 so that a light focusing region of the lens 46 is limited to only the core region Ga. Then, the opening of the adjustable diaphragm 47D is changed in accordance with the core region Ga to reliably prevent light from entering the core 57 that is not in use. As a result, light is emitted from only a single core 57 located at the core region Ga at the end face 56D of the illumination fiber 5D.

Figure 15:
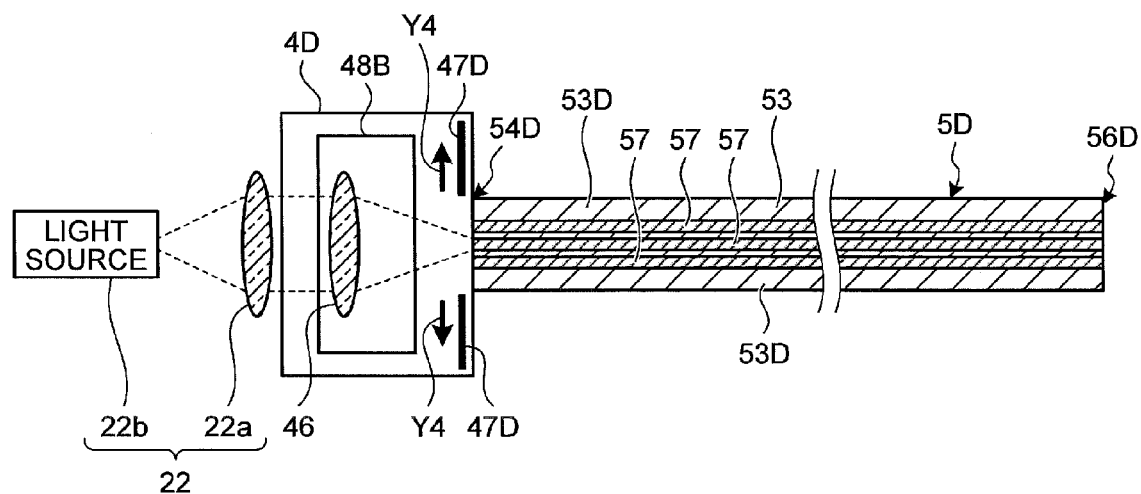
FIG. 15 is a diagram for explaining the switching unit illustrated in FIG. 13.

When the spatial coherence length of the illumination light is reduced, the moving system 48B moves the position of the lens 46 on the optical axis toward the illumination fiber 5D side as indicated by an arrow Y3 in FIG. 13 so that the light focusing region of the lens 46 corresponds to the core regions Ga and Gb. Then, as indicated by an arrow Y4 in FIG. 15, the opening of the adjustable diaphragm 47D is changed in accordance with the core regions Ga and Gb. As a result, light is emitted from the plurality of cores 57 located at the core regions Ga and Gb at the end face 56D of the illumination fiber 5D. When the spatial coherence length of the illumination light is further reduced, the position of the lens 46 on the optical axis and the opening region of the adjustable diaphragm 47D are adjusted so that the light focusing region of the lens 46 corresponds to the core regions Ga to Gc.

As in the third embodiment, even when a multicore fiber is used as the illumination fiber and the light focusing region on the illumination fiber is adjusted, similarly to the first embodiment, it is possible to perform illumination with a plurality of spatial coherence lengths by one probe.

Figure 16:
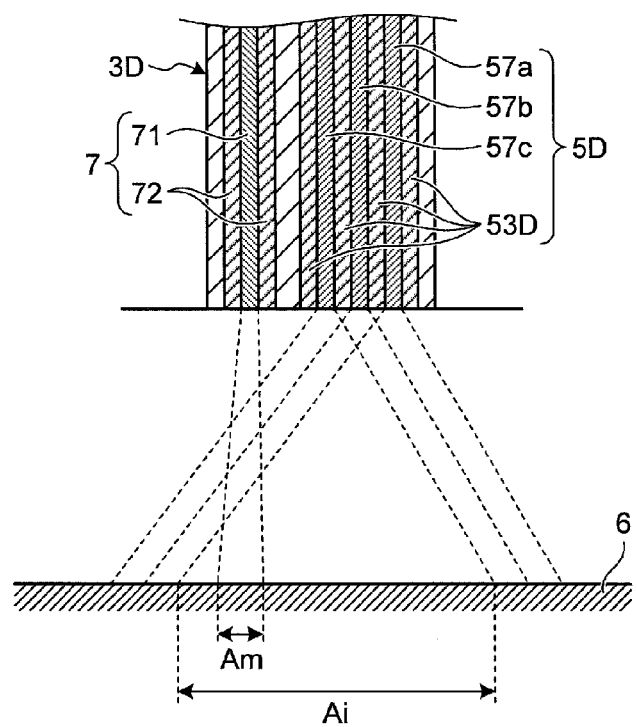
FIG. 16 is a cross-sectional view of the probe according to the third embodiment, taken along an optical axis.

In the third embodiment, the core diameters of the cores 57 are not necessarily the same but may differ from one another. When the switching unit 4D switches the region, in which light supplied by the light source unit 22 is input, to both the core regions Ga and Gb or to all the core regions Ga to Gc, each of which is formed of plurality of the cores 57, at least a part of illumination ranges of beams of light emitted from the plurality of the cores 57a to 57c of the illumination fiber 5D overlap each other in a region Ai as illustrated in FIG. 16, and a detection range Am of the detection fiber 7 provided in a same probe 3D is within the region Ai where the illumination regions overlap each other. This is because the spatial coherence length is reduced by all of the illumination fibers 57a to 57c in the region Ai but the spatial coherence length is not reduced by all of the illumination fibers 57a to 57c in the other illumination regions. Therefore, by appropriately setting a distance between the probe 3D and an object, the detection range Am is set to be within the region Ai in which the illumination regions overlap each other. Alternatively, it may be possible to use an optical system, such as a lens, at the tip of the probe 3D so that the overlapping region of the illumination regions and the detection region overlap each other on the surface of the object. The detection fiber 7 includes a core 71 and a cladding 72.

Figure 17:
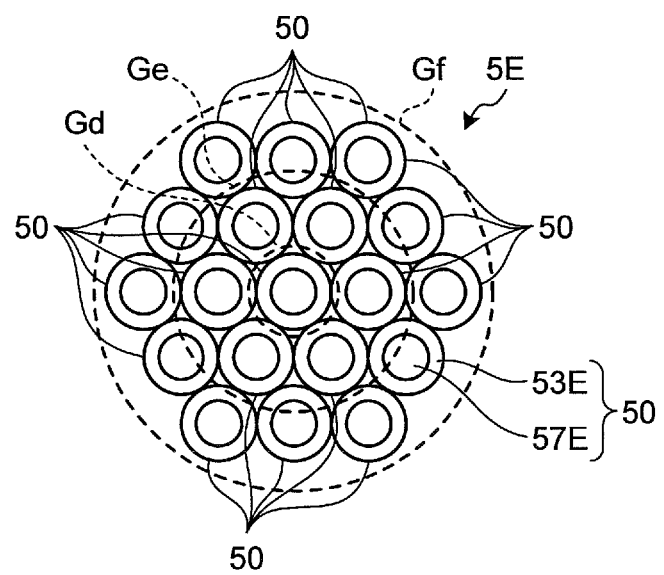
FIG. 17 is a diagram illustrating another example of the illumination fiber according to the third embodiment.

Furthermore, in the third embodiment, as illustrated in FIG. 17, it is possible to use, instead of the illumination fiber 5D, an illumination fiber 5E being an illumination fiber bundle formed of a plurality of fibers 50, each including a core 57E and a cladding 53E. FIG. 17 is a diagram illustrating the illumination fiber 5E viewed from the tip.

The switching unit 4D switches a fiber, in which light supplied by the light source unit 22 is input at a base end of the illumination fiber 5E, to one of the fibers or to one of a plurality of fiber groups, each including a different combination of a plurality of adjacent fibers. For example, the fibers 50 used for illumination are grouped into a fiber region Gd containing only one of the fibers 50, a fiber region Ge containing a plurality of the fibers 50 surrounding the fiber region Gd, and a fiber region Gf including a plurality of the fibers 50 surrounding the fiber region Ge. Then, the switching unit 4D switches the light focusing region on the illumination fiber 5E to the fiber region corresponding to a desired spatial coherence length. Even in this case, it is desirable that at least a part of illumination ranges of beams of light emitted from the plurality of the fibers 50 of the illumination fiber 5E overlap each other, and the detection range of the detection fiber provided in the same probe is within the region where the illumination regions overlap each other.

Fourth Embodiment

Figure 18:
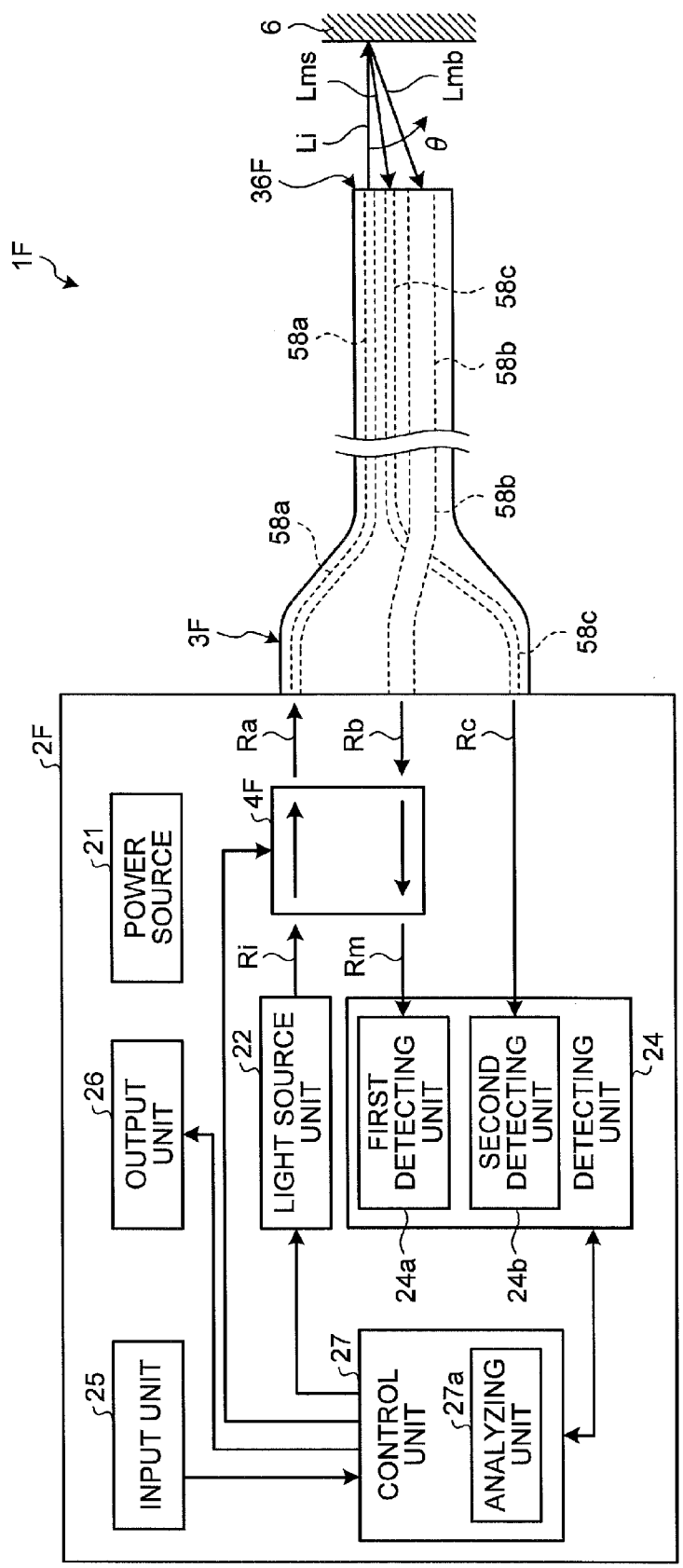
FIG. 18 is a schematic diagram of an overall configuration of an optical measurement apparatus according to a fourth embodiment.
Figure 19:
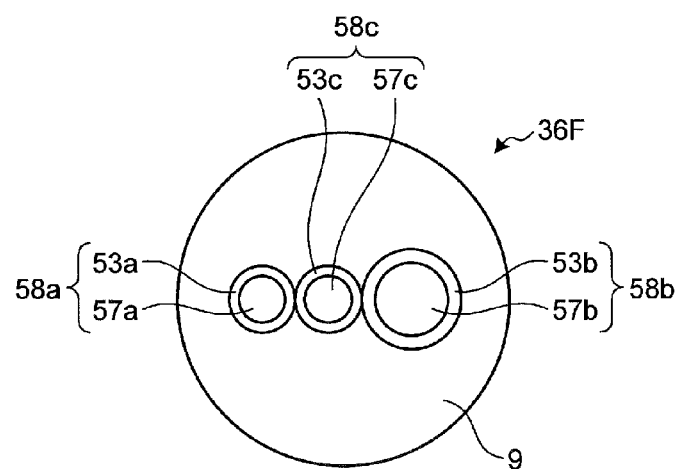
FIG. 19 is a diagram illustrating an end face of the illumination fiber illustrated in FIG. 18.

A fourth embodiment will be explained below. FIG. 18 is a schematic diagram of an overall configuration of an optical measurement apparatus according to the fourth embodiment. FIG. 19 is a diagram illustrating an end face of an illumination fiber illustrated in FIG. 18.

As illustrated in FIG. 18, an optical measurement apparatus 1F according to the fourth embodiment includes, compared with the optical measurement apparatus illustrated in FIG. 1, a main unit 2F including a switching unit 4F, instead of the main unit 2; and a probe 3F including shared fibers 58a and 58b and a detection fiber 58c, instead of the probe 3.

As illustrated in FIG. 19, the shared fibers 58a and 58b and the detection fiber 58c includes cores 57a to 57c and claddings 53a to 53c, respectively. The shared fibers 58a and 58b have functions of both the illumination fiber and the detection fiber. A core diameter of the shared fiber 58a is smaller than a core diameter of the shared fiber 58b. The side surfaces of all of the fibers are coated with a protection member 9.

Figure 20:
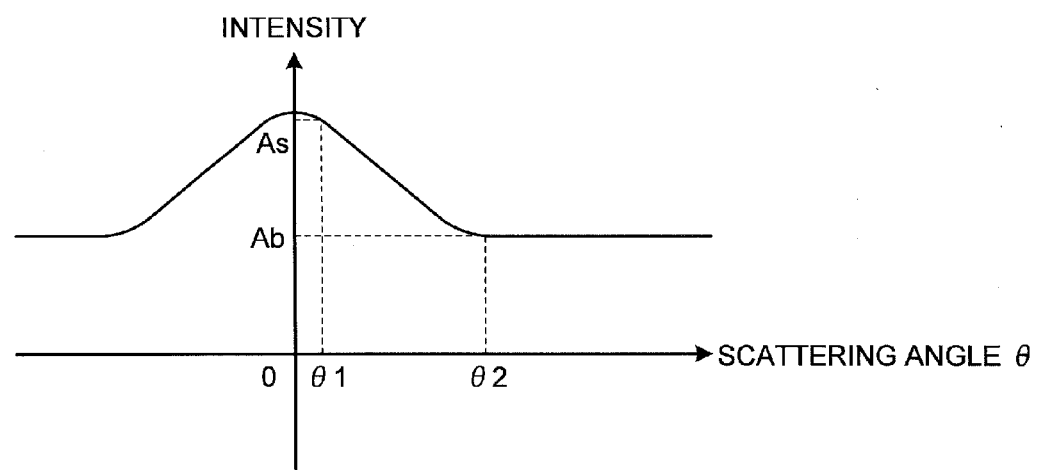
FIG. 20 is a diagram for explaining scattered light acquired by the optical measurement apparatus according to an embodiment.

When the LEBS technology is used, as illustrated in FIG. 20, a peak value As of an interference component of scattered light and a base value Ab of a base line that does not contribute to interference are acquired to perform analysis; therefore, it is necessary to receive scattered light with at least two different scattering angles. For example, to acquire the peak value As of the interference component of the scattered light, a scattered light with a scattering angle $\theta 1$ of approximately 0° is received. The scattered light with the scattering angle $\theta 1$ is received by a fiber adjacent to the illumination fiber. Furthermore, to acquire the base value Ab of the base line, a scattered light with a scattering angle $\theta 2$ of at least 1° or greater is received. The scattered light with the scattering angle $\theta 2$ is received by a fiber that is separate from the illumination fiber.

In the fourth embodiment, the switching unit 4F switches an output destination of light supplied by the light source unit 22 to a base end of one of the shared fibers 58a and 58b having the different core diameters in order to use the one of the shared fibers 58a and 58b as the illumination fiber. The switching unit 4F switches an output destination of light output from a base end of the other one of the shared fibers to the detecting unit 24 in order to use the other one of the shared fibers as a detection fiber. Therefore, scattered light with two different scattering angles can be received. As illustrated in FIG. 19, the detection fiber 58c is in contact with both the shared fibers 58a and 58b used as the illumination fibers; therefore, the detection fiber 58c receives scattered light with the scattering angle $\theta 1$ corresponding to the peak value As of the interference component of the scattered light both when the shared fiber 58a is used as the illumination fiber and when the shared fiber 58b is used as the illumination fiber.

The switching unit 4F switches, as illustrated in FIG. 18, a connection destination of a path Ri, to which light is output by the light source unit 22, to a path Ra connected to the base end of the shared fiber 58a or to a path Rb connected to the base end of the shared fiber 58b, and also switches a connection destination of a path Rm connected to a first detecting unit 24a of the detecting unit 24 to the path Ra or the path Rb that is not connected to the path Ri.

For example, as illustrated in FIG. 18, an example will be explained in which the switching unit 4F switches the connection destination of the path Ri to which the light is output by the light source unit 22 to the path Ra connected to the base end of the shared fiber 58a, and switches the connection destination of the path Rm connected to the first detecting unit 24a of the detecting unit 24 to the path Rb connected to the base end of the shared fiber 58b.

In this case, the light supplied by the light source unit 22 enters the base end of the shared fiber 58a via the path Ra. Therefore, the shared fiber 58a functions as the illumination fiber, and the light that has entered the base end of the shared fiber 58a propagates through the core 57a of the shared fiber 58a and is emitted as light Li from the tip of the shared fiber 58a at an end face 36F. Because the core diameter of the shared fiber 58a is smaller than the core diameter of the shared fiber 58b, the emission region of the light Lib becomes smaller than the case that the light is emitted from the shared fiber 58b. Therefore, the spatial coherence length of the light applied to the object 6 becomes longer than the spatial coherence length of the light emitted from the shared fiber 58b.

Figure 21:
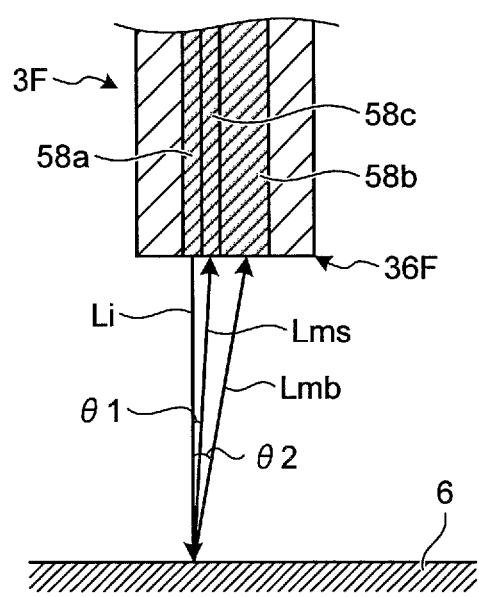
FIG. 21 is a cross-sectional view of the probe illustrated in FIG. 18, taken along an optical axis.

As illustrated in FIG. 21, at the end face 36F of the probe 3F, scattered light Lms with the scattering angle θ1 corresponding to the light Li emitted from the shared fiber 58a enters the tip of the detection fiber 58c being in contact with the shared fiber 58a. The light output from the base end of the detection fiber 58c is output to a second detecting unit 24b via the path Rc and is detected by the second detecting unit 24b. On the other hand, the scattering angle Lmb with the scattering angle θ2 enters the shared fiber 58b separated from the shared fiber 58a. The light output from the base end of the shared fiber 58b is output to the first detecting unit 24a via the path Rb and the path Rm that has been connected to the path Rb by the switching unit 4F and is detected by the first detecting unit 24a.

Figure 22:
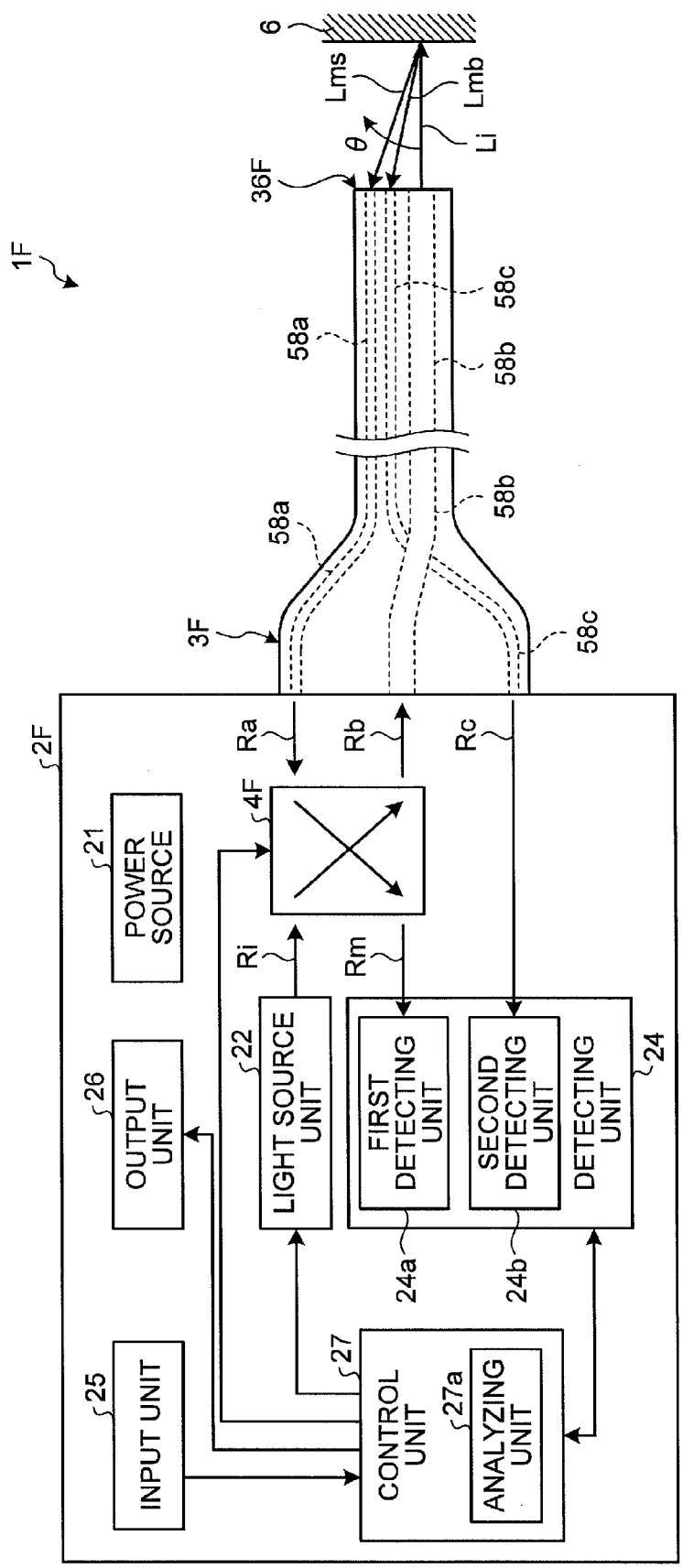
FIG. 22 is a diagram for explaining a switching unit illustrated in FIG. 18.

As illustrated in FIG. 22, an example will be explained in which the switching unit 4F switches the connection destination of the path Ri, to which the light is output by the light source unit 22, to the path Rb connected to the base end of the shared fiber 58b, and switches the connection destination of the path Rm connected to the first detecting unit 24a of the detecting unit 24 to the path Ra connected to the base end of the shared fiber 58a.

In this case, the light supplied by the light source unit 22 enters the base end of the shared fiber 58b via the path Rb. Therefore, the shared fiber 58b functions as the illumination fiber, and the light that has entered the base end of the shared fiber 58b propagates through the core 57b of the shared fiber 58b and is emitted as the light Li from the tip of the shared fiber 58b at the end face 36F. Because the core diameter of the shared fiber 58b is greater than the core diameter of the shared fiber 58a, the emission region of the light Lib becomes greater than the case that the light is emitted from the shared fiber 58a. Therefore, the spatial coherence length of the light applied to the object 6 becomes shorter than the spatial coherence length of the light emitted from the shared fiber 58a.

Figure 23:
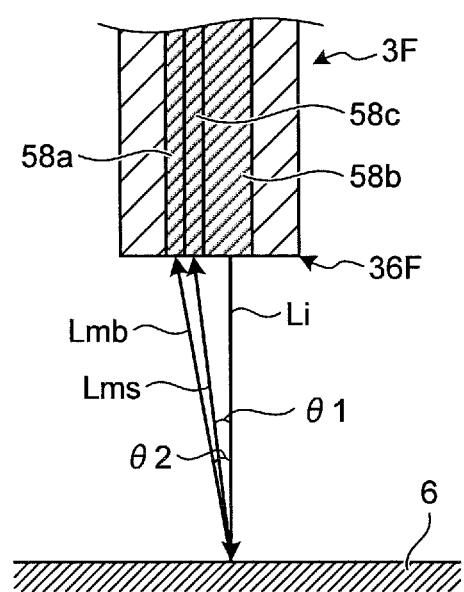
FIG. 23 is a diagram illustrating another example of the cross-section of the probe illustrated in FIG. 18, taken along the optical axis.

As illustrated in FIG. 23, at the end face 36F of the probe 3F, the scattered light Lms with the scattering angle θ1 corresponding to the light Li emitted from the shared fiber 58b enters the tip of the detection fiber 58c being in contact with the shared fiber 58b. The light output from the base end of the detection fiber 58c is output to the second detecting unit 24b via the path Rc and is detected by the second detecting unit 24b. On the other hand, the scattering angle Lmb with the scattering angle θ2 enters the shared fiber 58a separated from the shared fiber 58b. The light output from the base end of the shared fiber 58a is output to the first detecting unit 24a via the path Ra and the path Rm that has been connected to the path Ra by the switching unit 4F and is detected by the first detecting unit 24a.

Figure 24:
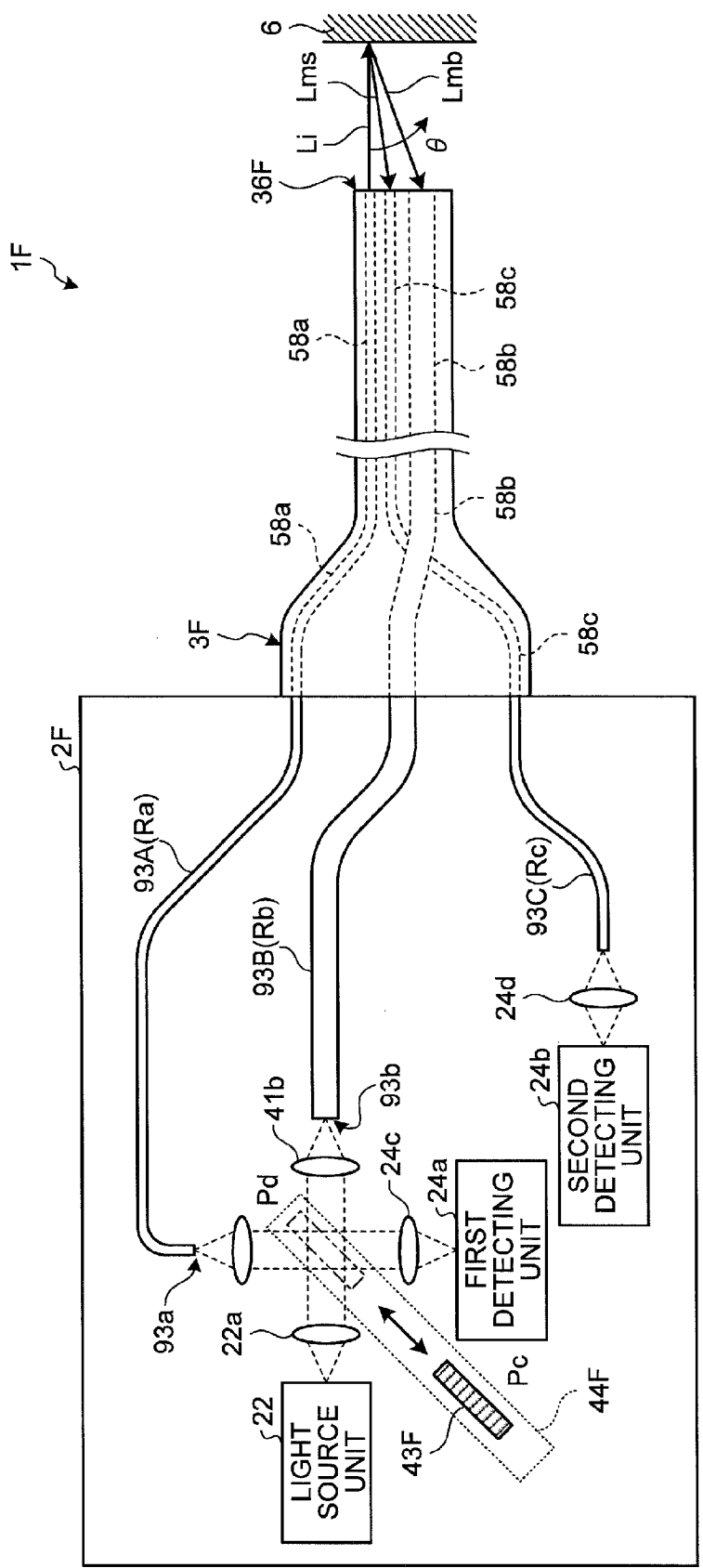
FIG. 24 is a diagram for explaining the switching unit illustrated in FIG. 18.

The switching unit 4F will be explained below. As illustrated in FIG. 24, a base end 93a of a connection fiber 93A that forms the path Ra and the first detecting unit 24a are disposed opposite each other, and the light source unit 22, a base end 93b of a connection fiber 93B that forms the path Rb, and the second detecting unit 24b are disposed opposite each other. The path between the base end 93a of the connection fiber 93A and the first detecting unit 24a and the path between the base end 93b of the connection fiber 93B and the light source unit 22 cross each other. Light output from a connection fiber 93C that forms the path Rc is output to the second detecting unit 24b via a lens 24d. In FIG. 24, illustrations of the other components of the main unit 2F are omitted.

The switching unit 4F includes a both side mirror 43F; and a moving system 44F including an actuator or the like for moving the both side mirror 43F. A moving system 44F moves the both side mirror 43F to a crossing position Pd, at which the path between the base end 93a of the connection fiber 93A and the first detecting unit 24a and the path between the base end 93b of the connection fiber 93B and the light source unit 22 cross each other, or an evacuation position Pc outside the paths.

When the moving system 44F evacuates the both side mirror 43F to the evacuation position Pc, light supplied by the light source 22b enters the opposing base end 93b of the connection fiber 93B via the lenses 22a and 41b and is supplied to the shared fiber 58b through the connection fiber 93B. Therefore, at the end face 36F of the probe 3F, the light Li is emitted from the shared fiber 58b having the core diameter greater than the core diameter of the shared fiber 58a. At the end face 36F of the probe 3F, the scattered light Lmb with the scattering angle θ2 enters the tip of the shared fiber 58a and then enters the first detecting unit 24a via the connection fiber 93A and lenses 41a and 24c.

On the other hand, when the moving system 44F moves the both side mirror 43F to the crossing position Pd, light supplied by the light source 22b via the lens 22a is reflected by one reflecting surface of the both side mirror 43F and enters the base end 93a of the connection fiber 93A. The light supplied from the connection fiber 93A to the shared fiber 58a is emitted as the light Li from the shared fiber 58a having the core diameter smaller than the core diameter of the shared fiber 58b at the end face 36F of the probe 3F. At the end face 36F of the probe 3F, the scattered light Lmb with the scattering angle θ2 corresponding to the base line value among the beams of the scattered light of the light Li emitted from the shared fiber 58a enters the tip of the shared fiber 58b. Then, the scattered light Lmb is reflected by other reflecting surface of the both side mirror 43F and enters the first detecting unit 24a through the connection fiber 93B and the lens 41b.

As described above, the optical measurement apparatus 1F according to the fourth embodiment employs the shared fibers 58a and 58b having different incident-emission regions for inputting or outputting light at the end face 36F. The optical measurement apparatus 1F causes the switching unit 4F to switch a fiber, in which light supplied by the light source unit 22 enters, to one of the shared fibers 58a and 58b at the base ends of the shared fibers 58a and 58b, and also switches an output destination of the returned light from the other shared fiber to the detecting unit 24. Therefore, according to the fourth embodiment, similarly to the first embodiment, it is possible to perform illumination with a plurality of coherence lengths by one probe.

In the fourth embodiment, the fiber in which the light supplied by the light source unit 22 enters is switched to one of the shared fibers 58a and 58b by using the switching unit 4F of the main unit 2F, and the output destination of the returned light from the other shared fiber is switched to the detecting unit 24; however, it is not limited thereto.

For example, a probe 3G illustrated in FIG. 25 will be explained. The probe 3G illustrated in FIG. 25 includes a connector 59 that can connect the base ends of the shared fibers 58a and 58b and the detection fiber 58c respectively to an output portion at which light supplied by the light source unit 22 of the main unit 2 is output and input portions at which light is input toward the first detecting unit 24a and the second detecting unit 24b. As illustrated in FIG. 26, at an end face 36G of the probe 3G, the fibers are disposed in the order of the shared fiber 58a, the detection fiber 58c, and the shared fiber 58b from the left in FIG. 26.

The connector 59 is inserted into an insertion port of a main unit 2G to thereby connect the output portion, at which the light from the light source unit 22 of the main unit 2 is output, to the base end of one of the shared fibers 58a and 58b at a contact surface. In addition, the connector 59 connects the base end of the other one of the shared fibers to the input portion, at which light is input toward the detecting unit 24 of the main unit 2G, at the contact surface. The connector 59 can be inserted into the main unit 2G such that the contact surface in contact with the light input and output portions of the main unit 2G is vertically inverted from the state illustrated in FIG. 25.

Figure 25:
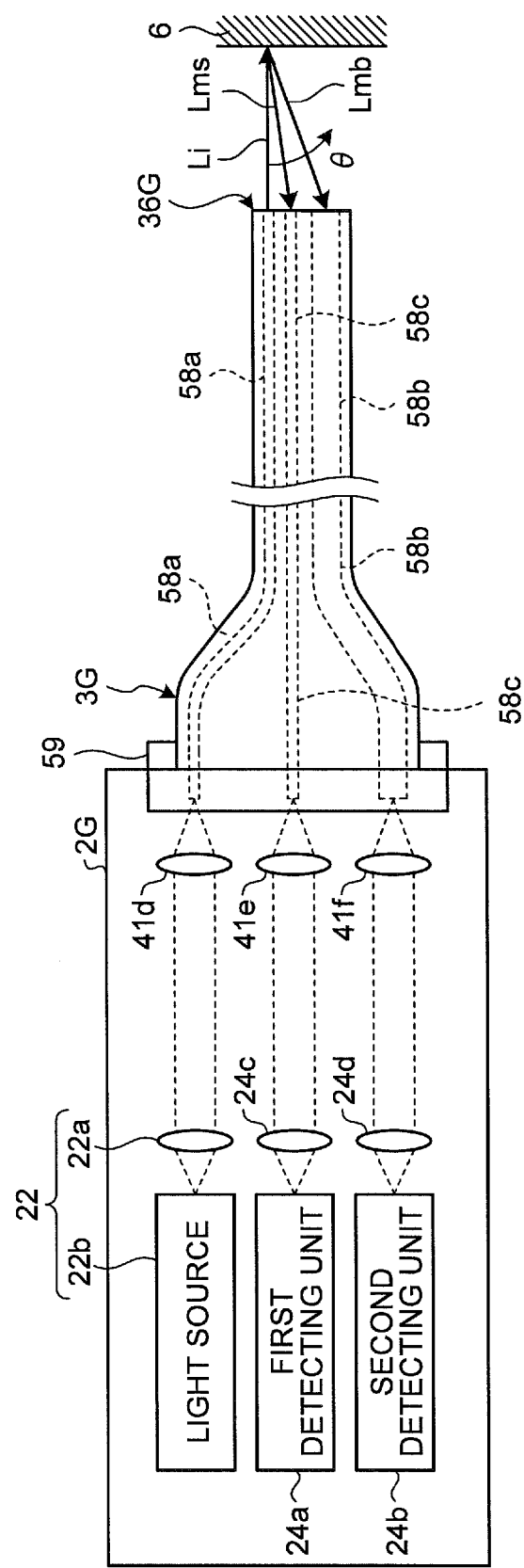
FIG. 25 is a schematic diagram of another overall configuration of the optical measurement apparatus according to the fourth embodiment.
Figure 26:
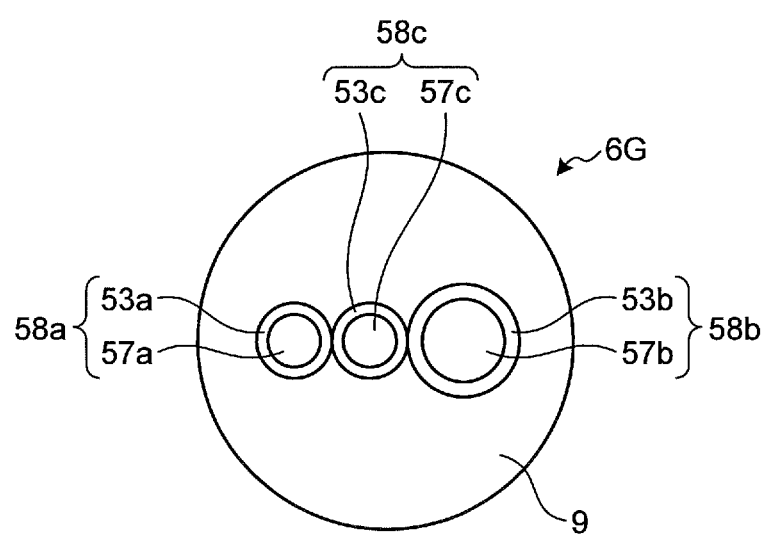
FIG. 26 is a diagram illustrating an end face of a probe illustrated in FIG. 25.

For example, when the connector 59 is inserted in the main unit 2G as illustrated in FIG. 25, light output by the light source 22b enters the base end of the shared fiber 58a via the lens 22a and a lens 41d. Therefore, the shared fiber 58a functions as the illumination fiber and emits the light Li from the end face 36G of the probe 3G. At the end face 36G of the probe 3G, the scattered light Lms with the scattering angle θ1 enters the tip of the detection fiber 58c being in contact with the shared fiber 58a, is output from the base end of the detection fiber 58c to the main unit 2G, and is output to the first detecting unit 24a via a lens 41e and the lens 24c. The scattering angle Lmb with the scattering angle θ2 enters the shared fiber 58b separated from the shared fiber 58a, is output from the base end of the shared fiber 58b to the main unit 2G, and is output to the second detecting unit 24b via the a lens 41f and the lens 24d.

Figure 27:
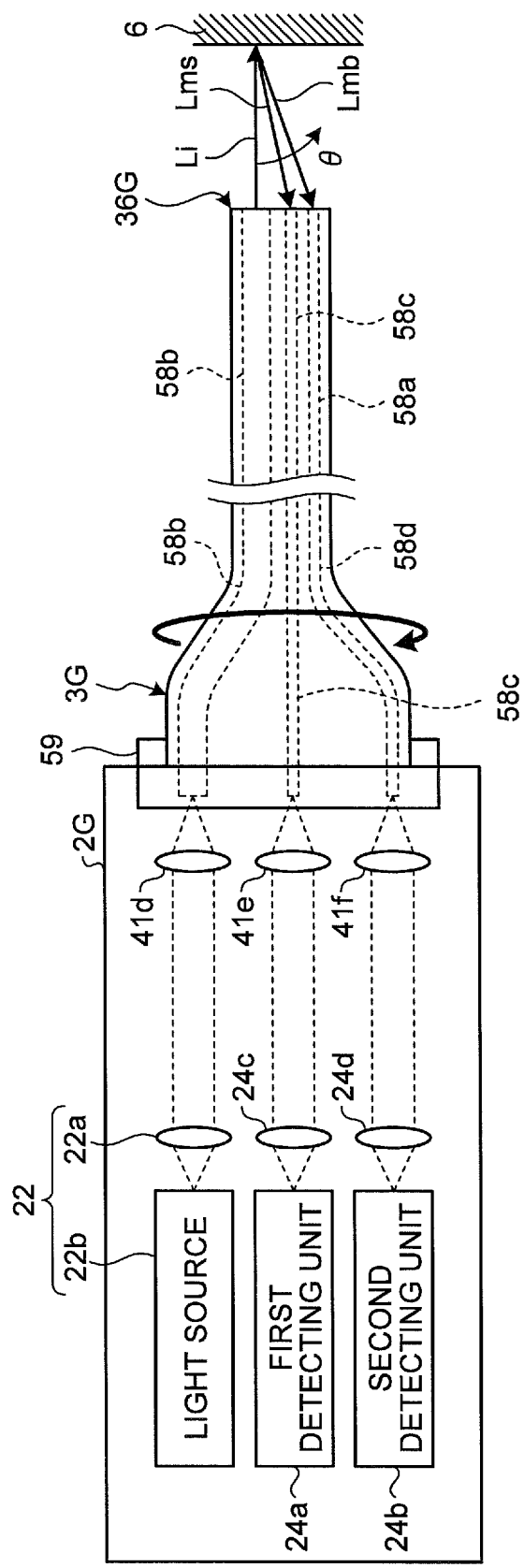
FIG. 27 is a diagram for explaining switching between fibers of the optical measurement apparatus illustrated in FIG. 25.

A case will be explained that the connector 59 is inserted into the main unit 2G such that the contact surface of the connector 59 is vertically inverted as indicated by an arrow in FIG. 27 compared with the state illustrated in FIG. 25. In this case, light output by the light source 22b enters the base end of the shared fiber 58b via the lenses 22a and 41d. Therefore, the shared fiber 58b functions as the illumination fiber and applies the light Li from the end face 36G of the probe 3G. At the end face 36G of the probe 3G, the scattered light Lms with the scattering angle θ1 enters the tip of the detection fiber 58c being in contact with the shared fiber 58b, is output from the base end of the detection fiber 58c to the main unit 2G, and is output to the first detecting unit 24a via the lenses 41e and 24c. The scattering angle Lmb with the scattering angle θ2 enters the shared fiber 58a separated from the shared fiber 58b, is output from the base end of the shared fiber 58a to the main unit 2G, and is output to the second detecting unit 24b via the lenses 41f and 24d.

Therefore, by changing the orientation of the contact surface of the connector 59 that comes in contact with the light output portion and the light input portion of the main unit 2G, the shared fiber connected to the light output portion of the light source unit 22 of the main unit 2G and the shared fiber connected to the light input portion of the detecting unit 24 of the main unit 2G are interchanged with each other. In FIG. 25 and FIG. 27, illustrations of the other components of the main unit 2G are omitted.

Figure 28:
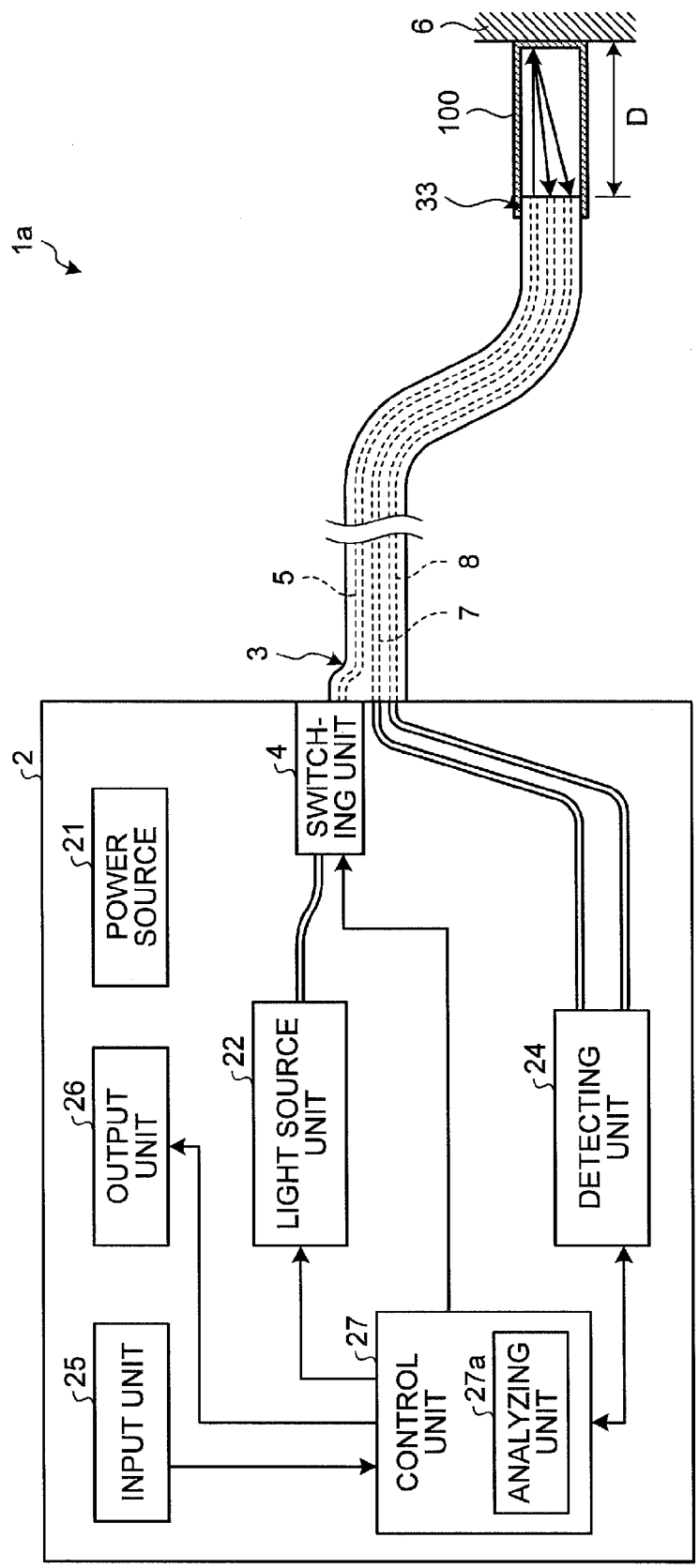
FIG. 28 is a schematic diagram of another overall configuration of the optical measurement apparatus according to the first embodiment.

In the probe according to the first to the fourth embodiments, as in an optical measurement apparatus 1a illustrated in FIG. 28, it may be possible to provide a single cap 100 on the tip portion 33 of the probe 3 for covering the tip of the illumination fiber 5 and the tips of the detection fibers 7 and 8. A surface of the cap 100 to be in contact with the object 6 is transparent. By bringing the cap 100 in contact with the object 6 to perform measurement, a distance D between the illumination fiber 5 and the object can be fixed by the cap 100; therefore it becomes possible to reliably fix the spatial coherence length of the illumination light during the measurement. Furthermore, the surface of the object 6 becomes flat by the bottom surface of the cap 100, so that the measurement can be performed without being influenced by irregularities of the surface of the object 6.

Figure 29:
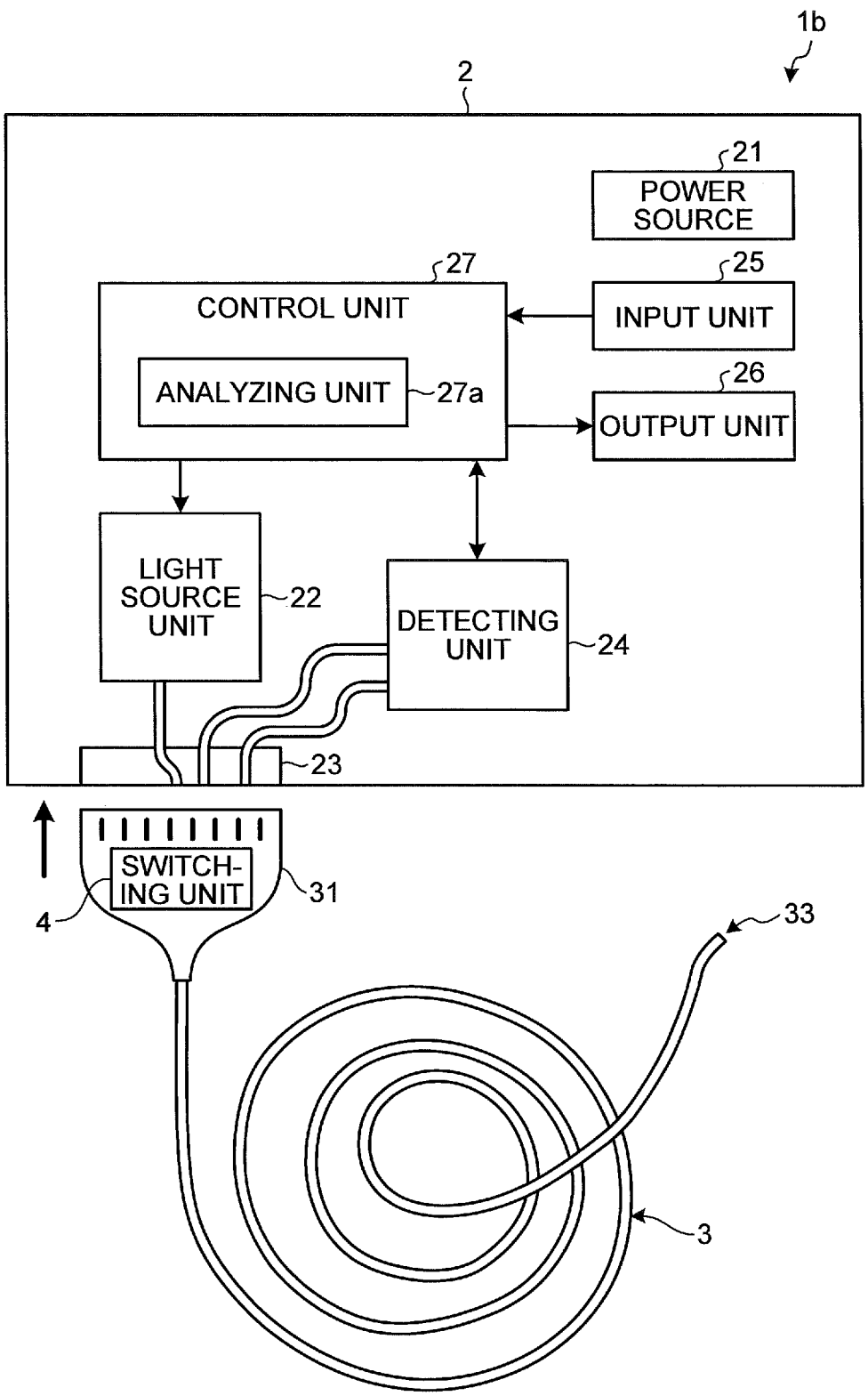
FIG. 29 is a schematic diagram of another overall configuration of the optical measurement apparatus according to the first embodiment.

Furthermore, in the first to the fourth embodiments, examples are explained in which the switching unit 4, 4A to 4D, or 4F is provided on the main unit 2, 2F, or 2G. However, as in the optical measurement apparatus 1b illustrated in FIG. 29, the switching unit may be provided on a probe 3. For example, in the example illustrated in FIG. 29, the switching unit 4 is provided on a base end portion 31 of the probe 3b that is detachably connected to a connection portion 23 of the main unit 2.

Moreover, in the first to the fourth embodiments, an example is explained that the illumination fiber is switched at the base end side of the probe. However, it is possible to provide an adjustable diaphragm at the tip of the probe, and switch the light output region of a single illumination fiber by changing the amount of opening of the adjustable diaphragm.

Fifth Embodiment

Figure 30:
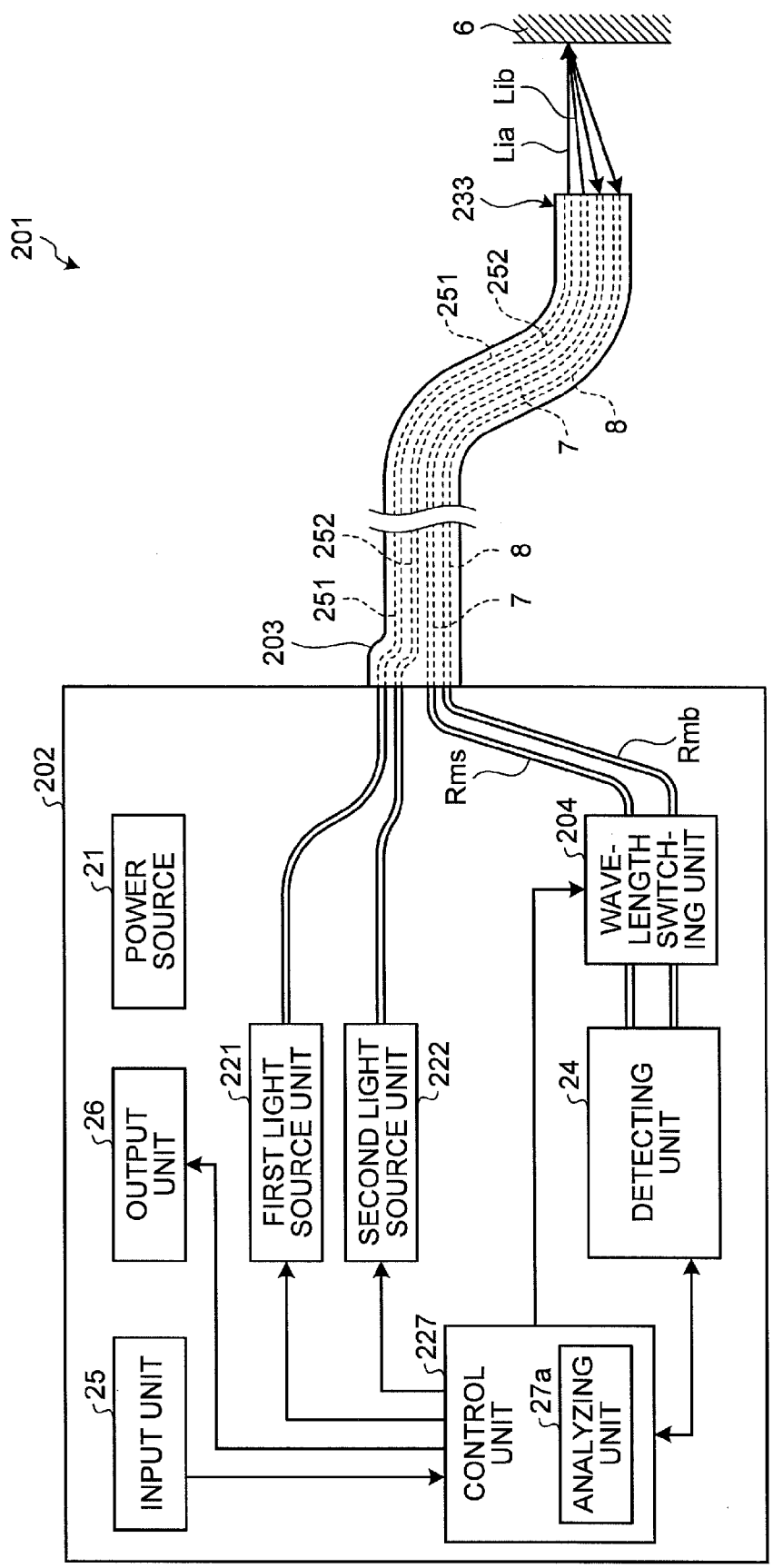
FIG. 30 is a schematic diagram of an overall configuration of an optical measurement apparatus according to a fifth embodiment.

A fifth embodiment will be explained below. In the fifth embodiment, an example will be explained in which a switching unit is disposed between a probe and a detecting unit. FIG. 30 is a schematic diagram of an overall configuration of an optical measurement apparatus according to the fifth embodiment.

As illustrated in FIG. 30, an optical measurement apparatus 201 according to the fifth embodiment includes a main unit 202 instead of the main unit 2 illustrated in FIG. 1; and a probe 203 instead of the probe 3. The main unit 202 includes, instead of the light source unit 22 of the main unit 2 illustrated in FIG. 1, a first light source unit 221 that emits light with a wavelength λ1; and a second light source unit 222 that emits light with a wavelength λ2 different from the wavelength λ1. The first light source unit 221 and the second light source unit 222 may be formed of wavelength filters with white light sources or may be formed of LEDs that emit beams of light with the wavelengths λ1 and λ2. The light source unit 221 and the light source unit 222 always emit illumination light. The main unit 202 does not include the switching unit 4 of the main unit 2, but includes a wavelength switching unit 204. A control unit 227 has the same functions as those of the control unit 27 illustrated in FIG. 1, and controls the first light source unit 221, the second light source unit 222, and the wavelength switching unit 204. The first light source unit 221 and the second light source unit 222 are incoherent light sources.

The probe 203 includes illumination fibers 251 and 252 having different core diameters, instead of the illumination fiber 5 illustrated in FIG. 1. The illumination fibers 251 and 252 have the base end of the probe 203 and a tip 233.

Figure 31:
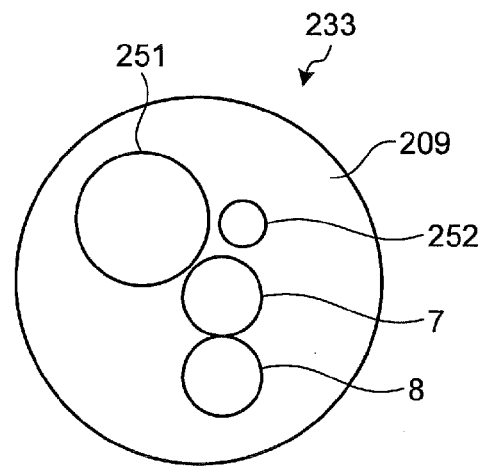
FIG. 31 is a diagram illustrating an end face of a probe illustrated in FIG. 30.

FIG. 31 is a diagram illustrating an end face of the probe 203 illustrated in FIG. 30. In the example illustrated in FIG. 31, the illumination fiber 251 has a greater emission region at the tip 233 than that of the illumination fiber 252. Therefore, the area of the emission region in which light is emitted at the tip 233 differs between the illumination fiber 251 and the illumination fiber 252. The side surfaces of all of the fibers are coated with a protection member 209.

The illumination fiber 251 is connected to the first light source unit 221 at the base end thereof, and emits light Lia with the wavelength $\lambda 1$ from the tip 233 of the probe 203. The illumination fiber 252 is connected to the second light source unit 222 at the base end thereof, and emits light Lib with the wavelength $\lambda 2$ from the tip 233 of the probe 203. The area of the emission region of the illumination fiber 251 is greater than that of the illumination fiber 252 at the tip 233; therefore, the light Lia with the wavelength $\lambda 1$ emitted from the illumination fiber 251 connected to the first light source unit 221 has a relatively short spatial coherence length. On the other hand, the light Lib with the wavelength $\lambda 2$ emitted from the illumination fiber 252 connected to the second light source unit 222 has a relatively long spatial coherence length.

The detection fiber 7 is disposed close to both the illumination fibers 251 and 252 and receives scattered light with the scattering angle $\theta 1$ corresponding to the peak value As of an interference component of the scattered light. The detection fiber 8 is separated from both the illumination fibers 251 and 252 and receives scattered light with the scattering angle $\theta 2$ corresponding to the base value Ab at the base line of the scattered light. Each scattered light includes both the light with the wavelength $\lambda 1$ and the light with the wavelength $\lambda 2$.

Figure 32:
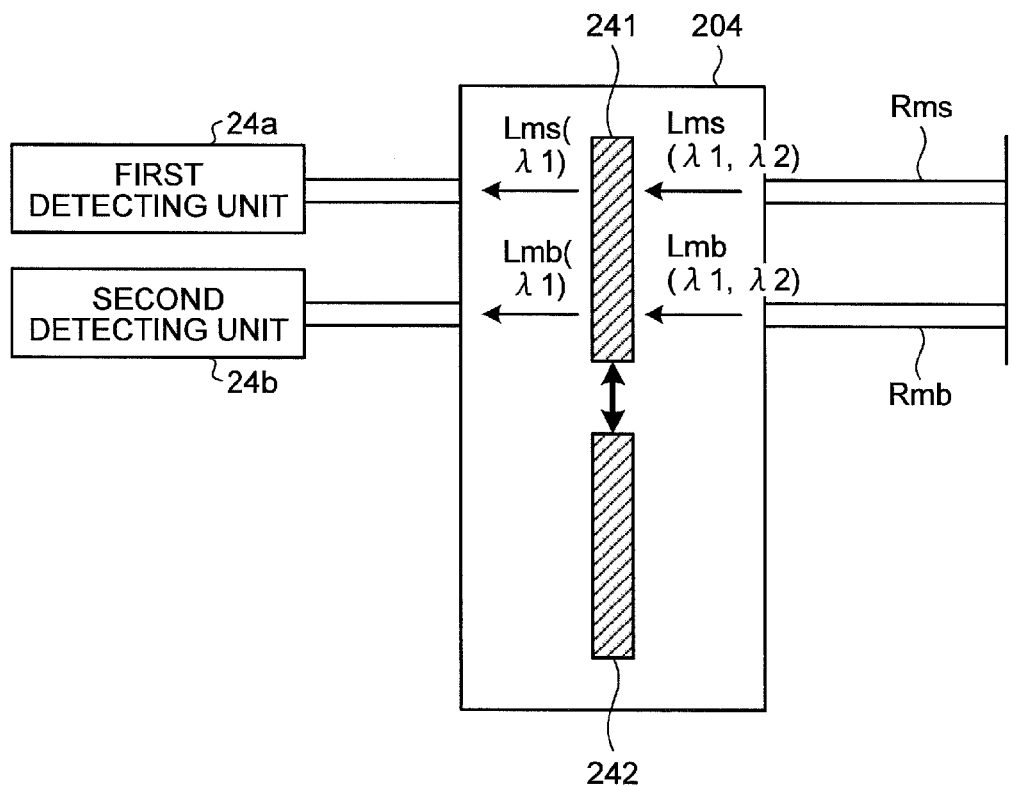
FIG. 32 is a diagram for explaining a wavelength switching unit illustrated in FIG. 30.

The wavelength switching unit 204 has a function of selectively switching to the wavelength $\lambda 1$ or the wavelength $\lambda 2$ between the beams of light with the wavelengths $\lambda 1$ and $\lambda 2$ to be input to the first detecting unit 24a and the second detecting unit 24b. As illustrated in FIG. 32, the wavelength switching unit 204 switches between a wavelength filter 241 that transmits only light with the wavelength $\lambda 1$ and a wavelength filter 242 that transmits only light with the wavelength $\lambda 2$.

First, a case will be explained in which the wavelength filter 241 is attached to the wavelength switching unit 204. In this case, light Lms with the scattering angle $\theta 1$ is output from the detection fiber 7 and input to the wavelength switching unit 204 via a path Rms. Through the wavelength filter 241, only the light with the wavelength $\lambda 1$ of the light Lms with the scattering angle $\theta 1$ is output from the wavelength switching unit 204 and detected by the first detecting unit 24a. Furthermore, light Lmb with the scattering angle $\theta 2$ is output from the detection fiber 8 and input to the wavelength switching unit 204 via a path Rmb. Through the wavelength filter 241, only the light with the wavelength $\lambda 1$ of the light Lmb with the scattering angle $\theta 2$ is output from the wavelength switching unit 204 and detected by the second detecting unit 24b.

A case will be explained in which the wavelength filter 242 is attached to the wavelength switching unit 204. In this case, through the wavelength filter 242, only the light with the wavelength $\lambda 2$ of the light Lms with the scattering angle $\theta 1$ output from the detection fiber 7 is output from the wavelength switching unit 204 and detected by the first detecting unit 24a. Furthermore, through the wavelength filter 242, the light with the wavelength $\lambda 2$ of the light Lmb with the scattering angle $\theta 2$ output from the detection fiber 8 is output from the wavelength switching unit 204 and detected by the second detecting unit 24b.

To acquire the scattered light corresponding to light with a relatively short spatial coherence length, because the core diameter of the illumination fiber 251 that outputs the light Lia with the wavelength $\lambda 1$ is greater than the core diameter of the illumination fiber 252, it is sufficient to switch to the wavelength filter 241 in the wavelength switching unit 204. On the other hand, to acquire the scattered light corresponding to light with a relatively long spatial coherence length, because the core diameter of the illumination fiber 252 that emits the light Lib with the wavelength $\lambda 2$ is smaller than the core diameter of the illumination fiber 251, it is sufficient to switch to the wavelength filter 242 in the wavelength switching unit 204.

In this way, even when beams of light with different wavelengths are applied by using a plurality of illumination fibers having different emission regions and the wavelength corresponding to light with a spatial coherence length to be acquired is selected in the output path of the scattered light, it is possible to perform illumination with a plurality of coherence lengths by one probe.

The wavelength switching unit 204 may be configured to electrically switch between the wavelengths by using a liquid crystal tunable filter or the like, instead of switching between the wavelength filters 241 and 242 as illustrated in FIG. 32.

Sixth Embodiment

Figure 33:
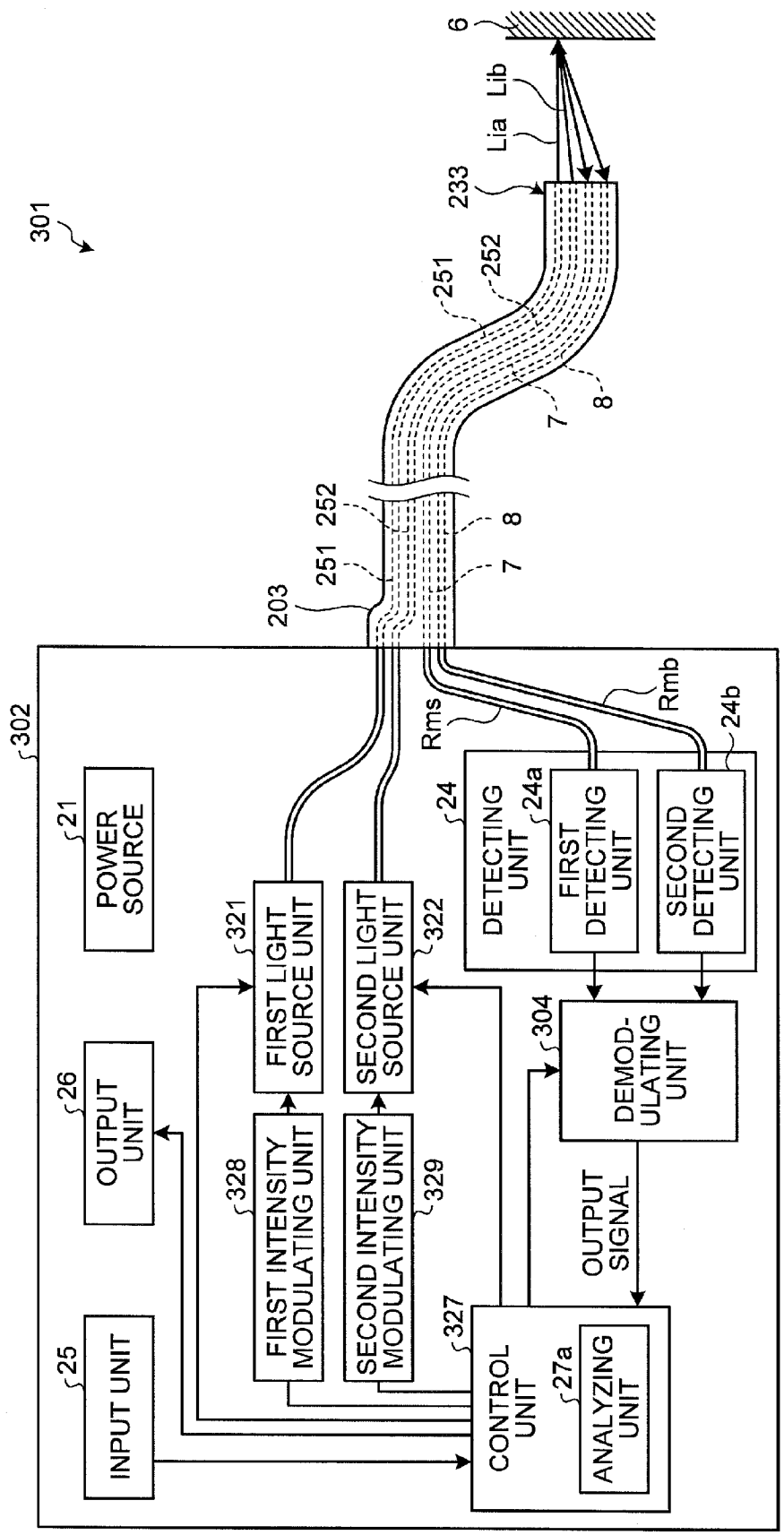
FIG. 33 is a schematic diagram of an overall configuration of an optical measurement apparatus according to a sixth embodiment.

A sixth embodiment will be explained below. FIG. 33 is a schematic diagram of an overall configuration of an optical measurement apparatus according to the sixth embodiment. As illustrated in FIG. 33, an optical measurement apparatus 301 according to the sixth embodiment includes a main unit 302 instead of the main unit 202 illustrated in FIG. 30.

The main unit 202 further includes, compared with the main unit 202 illustrated in FIG. 30, a first light source unit 321 connected to the base end of the illumination fiber 251; a second light source unit 322 connected to the base end of the illumination fiber 252; a first intensity modulating unit 328 connected to the first light source unit 321; a second intensity modulating unit 329 connected to the second light source unit 322; and a demodulating unit 304. Beams of the scattered light emitted from the base ends of the detection fibers 7 and 8 are directly output to the first detecting unit 24a and the second detecting unit 24b of the detecting unit 24, respectively. The demodulating unit 304 demodulates detection signals that are respectively output from the first detecting unit 24a and the second detecting unit 24b of the detecting unit 24 by using a selected frequency, and outputs the detection signals to the analyzing unit 27a as output signals. A control unit 327 has the same functions as those of the control unit 27 illustrated in FIG. 1, and controls the first light source unit 321, the second light source unit 222, the first intensity modulating unit 328, the second intensity modulating unit 329, and the demodulating unit 304. As the first light source unit 321 and the second light source unit 322, for example, a white light source that is an incoherent light source is used.

Figure 34:
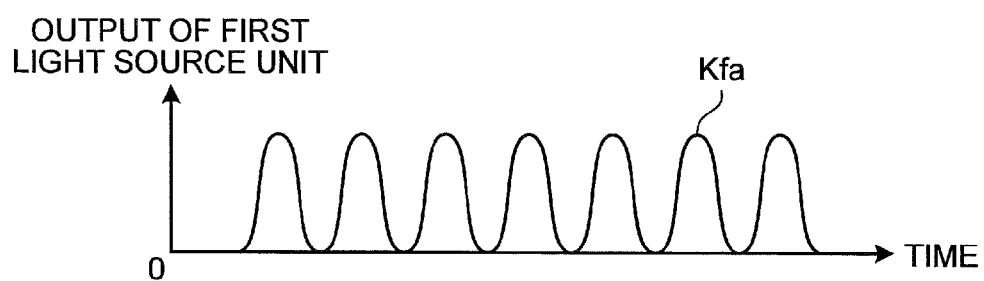
FIG. 34 is a diagram illustrating the time dependency of the intensity of light output by a first light source unit illustrated in FIG. 33.

The intensity of light output by the first light source unit 321 is modulated by the first intensity modulating unit 328. The first intensity modulating unit 328 sets a frequency fa as a modulation frequency, and modulates the intensity of the light output by the first light source unit 321 in accordance with the frequency fa so as to obtain a curve Kfa indicating the time dependency of the intensity of the output light as illustrated in FIG. 34.

The intensity of light output by the second light source unit 322 is modulated by the second intensity modulating unit

Figure 35:
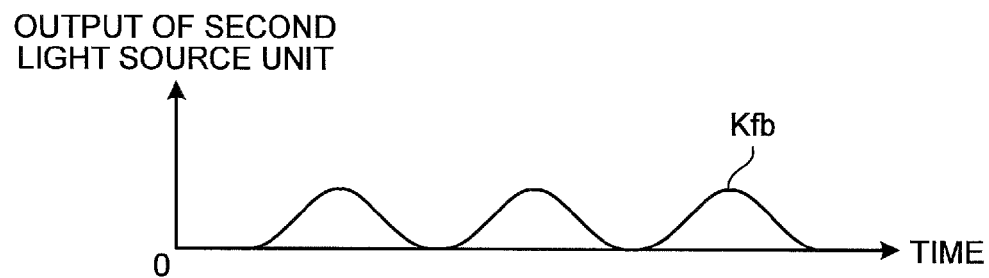
FIG. 35 is a diagram illustrating the time dependency of the intensity of light output by a second light source unit illustrated in FIG. 33.

329. The second intensity modulating unit 329 sets, as a modulation frequency, a frequency fb that is different from the frequency fa, and modulates the intensity of the light output by the second light source unit 322 in accordance with the frequency fb so as to obtain a curve Kfb indicating the time dependency of the intensity of the output light as illustrated in FIG. 35.

Similarly to the fifth embodiment, the area of the emission region of the illumination fiber 251 is greater than that of the illumination fiber 252 at the tip 233; therefore, the light Lia with the frequency fa output from the illumination fiber 251 connected to the first light source unit 321 has a relatively small spatial coherence. On the other hand, the light Lib with the frequency fb output from the illumination fiber 252 connected to the second light source unit 322 has a relatively large spatial coherence.

The demodulating unit 304 selects the frequency fa or the frequency fb used for the intensity modulation by the light source units under the control of the control unit 327, and extracts and outputs only a signal with the selected frequency component. For example, when the frequency fa is selected by the demodulating unit 304, the output signal from the demodulating unit 304 becomes a signal that is obtained when the scattered light is extracted by illuminating the object 6 with light having a relatively short spatial coherence length through the illumination fiber 251. On the other hand, when the frequency fb is selected by the demodulating unit 304, the output signal becomes a signal that is obtained when the scattered light is extracted by illuminating the object 6 with light with a relatively long spatial coherence length through the illumination fiber 252.

In this way, according to the sixth embodiment, it is possible to switch the spatial coherence length of light used for illumination by selecting the frequency f1 or the frequency f2 extracted by the demodulating unit 304. Therefore, it is possible to perform illumination with a plurality of spatial coherence lengths by one probe.

Furthermore, the optical measurement apparatuses according to the first to the sixth embodiments use the detecting unit 24; therefore, it is possible to perform various types of detection. The first to the sixth embodiments are not limited to the case using the LEBS technology, but can be applied to any measurement apparatus based on two different spatial coherence lengths.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical measurement apparatus that measures an optical property of a scattering medium, the optical measurement apparatus comprising:
   a light source configured to supply illumination light having at least one spectral component;
   an illumination fiber configured to guide the illumination light supplied by the light source and to emit the illumination light to the scattering medium;
   a detection fiber configured to receive returned light from the scattering medium at a tip of the detection fiber and to guide the returned light toward a base end of the detection fiber;
   a detecting unit configured to detect the returned light that is output from the base end of the detection fiber;
   a measuring unit configured to measure a property of the scattering medium based on a detection result obtained by the detecting unit; and
   a switching unit configured to change a spatial coherence length of the illumination light emitted from the scattering medium by switching a size of an emission area in which the illumination light is emitted at an end face of the illumination fiber.

2. The optical measurement apparatus according to claim 1, wherein:
   the illumination fiber includes a first light guide and a second light guide, the first light guide and the second light guide each having a different light emission region for emitting the illumination light at the end face, and
   the switching unit is configured to switch a region, in which the illumination light supplied by the light source is input, to one of the first light guide and the second light guide at a base end of the illumination fiber.

3. The optical measurement apparatus according to claim 1, wherein:
   the illumination fiber is a multi-cladding fiber including two or more cladding layers arranged around a core, and
   the switching unit is configured to switch a region, in which the illumination light supplied by the light source is input, to one of the core and a cladding that is in contact with the core at a base end of the illumination fiber.

4. The optical measurement apparatus according to claim 1, wherein:
   the illumination fiber is a multicore fiber including a plurality of cores, and
   the switching unit is configured to switch a region, in which the illumination light supplied by the light source is input, to one of the cores of the illumination fiber or to one of a plurality of core groups, each of the core groups including a different combination of a plurality of adjacent cores, at a base end of the illumination fiber.

5. The optical measurement apparatus according to claim 4, wherein when the switching unit is configured to switch the region in which the illumination light supplied by the light source is input to one of the core groups each including a plurality of cores, at least a part of illumination ranges of beams of the illumination light output by the cores overlap each other and a detection range of the detection fiber is within a region where the illumination ranges overlap each other.

6. The optical measurement apparatus according to claim 1, wherein:
   the illumination fiber is an illumination fiber bundle formed of a plurality of fibers, and
   the switching unit is configured to switch a fiber, in which the illumination light supplied by the light source is input, to one of the fibers or to one of a plurality of fiber groups, each of the fiber groups including a different combination of a plurality of adjacent fibers, at a base end of the illumination fiber.

7. The optical measurement apparatus according to claim 6, wherein:
   when the switching unit is configured to switch the region in which the illumination light supplied by the light source is input to one of the fiber groups, at least a part of illumination ranges of beams of the illumination light output by the fibers overlap each other and a detection range of the detection fiber is within a region where the illumination ranges overlap each other.

8. The optical measurement apparatus according to claim 1, wherein:

each of the illumination fiber and the detection fiber includes a plurality of shared fibers at an end face thereof, each of the shared fibers has an emission region with a different area for outputting and inputting illumination light, and the switching unit is configured to switch a fiber, in which the illumination light supplied by the light source is input, to one of the shared fibers at the base ends of the shared fibers and to switch an output destination of the returned light output from the other one of the shared fibers to the detecting unit.

9. The optical measurement apparatus according to claim 1, further comprising:
a main unit that includes the light source, the detecting unit, and the measuring unit; and
a probe that includes the illumination fiber and the detection fiber, that is detachably connected to the main unit, and that is insertable into a body.

10. The optical measurement apparatus according to claim 9, wherein the main unit includes the switching unit.

11. The optical measurement apparatus according to claim 9, wherein the probe includes the switching unit.

12. The optical measurement apparatus according to claim 1, further comprising a cap that covers a tip of the illumination fiber and the tip of the detection fiber.

13. The optical measurement apparatus according to claim 1, wherein the detecting unit is a spectroscope.

14. The optical measurement apparatus according to claim 1, wherein the light source is an incoherent light source.

15. An optical measurement apparatus that measures an optical property of a scattering medium, the optical measurement apparatus comprising:
a main unit; and
a probe that is detachably connected to the main unit and that is insertable into a body, wherein:
the main unit includes:
a light source that supplies illumination light having at least one spectral component;
a detecting unit that detects returned light from the scattering medium output by the probe; and
a measuring unit that measures a property of the scattering medium based on a detection result obtained by the detecting unit, and
the probe includes:
a plurality of shared fibers, each having an incident-emission region with a different area for inputting and outputting illumination light at an end face thereof; and
a connecting unit that is inserted into an insertion port of the main unit to connect an output portion of the main unit, at which the illumination light supplied by the light source is output, and a base end of one of the shared fibers, and to connect a base end of the other shared fiber and an input portion of the main unit, at which the returned light is input toward the detecting unit, wherein
an orientation of a contact face of the connecting unit being in contact with the output portion and the input portion of the main unit is changeable to switch between the shared fiber connected to the output portion of the main unit at which the illumination light supplied by the light source is output and the shared fiber connected to the input portion of the main unit at which the returned light is input toward the detecting unit.

16. The optical measurement apparatus according to claim 15, further comprising a cap that covers tips of the shared fibers.

17. The optical measurement apparatus according to claim 15, wherein the detecting unit is a spectroscope.

18. The optical measurement apparatus according to claim 15, wherein the light source is an incoherent light source.

19. A measurement probe apparatus that is detachably connected to an optical measurement apparatus that measures a property of a scattering medium, the measurement probe apparatus comprising:
an illumination fiber configured to guide illumination light supplied by an external apparatus and to emit the illumination light to the scattering medium;
a detection fiber configured to receive returned light from the scattering medium at a tip of the detection fiber and to guide the returned light to a base end of the detection fiber; and
a switching unit configured to change a spatial coherence length of the illumination light emitted from the scattering medium by switching a size of an emission area in which the illumination light is emitted at an end face of the illumination fiber.

20. The probe apparatus according to claim 19, wherein:
the illumination fiber includes a first light guide and a second light guide, each having a light emission region with a different area for emitting the illumination light at the end face, and
the switching unit is configured to switch a region, in which the illumination light supplied by the light source is input, to one of the first light guide and the second light guide at a base end of the illumination fiber.

21. The probe apparatus according to claim 19, wherein:
the illumination fiber is a multi-cladding fiber including two or more cladding layers arranged around a core, and
the switching unit is configured to switch a region, in which the illumination light supplied by the light source is input, to one of the core and a cladding being in contact with the core at a base end of the illumination fiber.

22. The probe apparatus according to claim 19, wherein:
the illumination fiber is a multicore fiber including a plurality of cores, and
the switching unit is configured to switch a region, in which the illumination light supplied by the light source is input, to one of the cores of the illumination fiber or to one of a plurality of core groups, each of the core groups including a different combination of a plurality of adjacent cores, at a base end of the illumination fiber.

23. The probe apparatus according to claim 22, wherein the switching unit is configured to switch a fiber, in which the illumination light supplied by the light source is input, to one of the fibers or to one of a plurality of fiber groups, each of the fiber groups including a different combination of a plurality of adjacent fibers, at a base end of the illumination fiber.

24. The probe apparatus according to claim 19, wherein:
the illumination fiber is an illumination fiber bundle formed of a plurality of fibers, and
the switching unit is configured to switch a fiber, in which the illumination light supplied by the light source is input, to one of the fibers or to one of a plurality of fiber groups, each of the fiber groups including a different combination of a plurality of adjacent fibers, at a base end of the illumination fiber.

25. The probe apparatus according to claim 24, wherein when the switching unit is configured to switch the region in which the illumination light supplied by the light source is input to one of the fiber groups, at least a part of illumination ranges of beams of the illumination light output by the fibers overlap each other and a detection range of the detection fiber is within a region where the illumination ranges overlap each other.

26. The probe apparatus according to claim 19, wherein:
each of the illumination fiber and the detection fiber includes a plurality of shared fibers at an end face thereof, each of the shared fibers has an emission region with a different area for outputting and inputting illumination light, and
the switching unit is configured to switch a fiber, in which the illumination light supplied by the light source is input, to one of the shared fibers at the base ends of the shared fibers and to switch an output destination of the returned light output from the other one of the shared fibers to the detecting unit.

27. The probe apparatus according to claim 19, further comprising a cap that covers a tip of the illumination fiber and the tip of the detection fiber.

* * * * *